(12) United States Patent
Nakatate

(10) Patent No.: US 11,147,435 B2
(45) Date of Patent: Oct. 19, 2021

(54) SUCTION CATHETER

(71) Applicant: FUJIKURA LTD., Tokyo (JP)

(72) Inventor: Kenichi Nakatate, Sakura (JP)

(73) Assignee: FUJIKURA LTD., Tokyo (JP)

( * ) Notice: Subject to any disclaimer, the term of this patent is extended or adjusted under 35 U.S.C. 154(b) by 766 days.

(21) Appl. No.: 14/223,417

(22) Filed: Mar. 24, 2014

(65) Prior Publication Data

US 2014/0288371 A1   Sep. 25, 2014

Related U.S. Application Data

(63) Continuation of application No. PCT/JP2012/078877, filed on Nov. 7, 2012.

(30) Foreign Application Priority Data

Nov. 7, 2011   (JP) .............................. JP2011-243784

(51) Int. Cl.
*A61B 1/04* (2006.01)
*A61B 1/267* (2006.01)
(Continued)

(52) U.S. Cl.
CPC .......... *A61B 1/042* (2013.01); *A61B 1/00052* (2013.01); *A61B 1/00105* (2013.01);
(Continued)

(58) Field of Classification Search
CPC ............ A61B 1/00045; A61B 1/00048; A61B 1/00052; A61B 1/00066; A61B 1/00094; A61B 1/00096; A61B 1/00105; A61B 1/00114; A61B 1/00117; A61B 1/00124; A61B 1/00126; A61B 1/0016; A61B 1/00163; A61B 1/00165; A61B 1/00167; A61B 1/0017; A61B 1/00172;
(Continued)

(56) References Cited

U.S. PATENT DOCUMENTS 5,873,814 A * 2/1999 Adair ................. A61B 1/00052
600/109
6,004,263 A * 12/1999 Nakaichi ............ A61B 1/00165
600/120
(Continued)

FOREIGN PATENT DOCUMENTS

GB   WO 2010089726 A2 *  8/2010  ......... A61B 1/00052
JP   2004-109222 A        4/2004
(Continued)

OTHER PUBLICATIONS

Communication dated May 21, 2015, issued by the State Intellectual Property Office of the People's Republic of China in counterpart Application No. 201280053058.1.
(Continued)

*Primary Examiner* — Ryan N Henderson
(74) *Attorney, Agent, or Firm* — Sughrue Mion, PLLC

(57) ABSTRACT

A suction catheter of the invention includes: a catheter main body that includes a suction passage along a longitudinal direction thereof; a control unit that is attached to an end portion of the catheter main body which is opposite to an operation portion; and an imaging unit that is attachable to and detachable from the control unit.

10 Claims, 17 Drawing Sheets

(51) Int. Cl.
*A61B 1/00* (2006.01)
*A61B 1/07* (2006.01)
*A61B 1/06* (2006.01)
*A61M 1/00* (2006.01)
*A61B 1/015* (2006.01)
*A61M 16/04* (2006.01)

(52) U.S. Cl.
CPC .......... *A61B 1/00165* (2013.01); *A61B 1/015* (2013.01); *A61B 1/0684* (2013.01); *A61B 1/07* (2013.01); *A61B 1/267* (2013.01); *A61M 1/742* (2021.05); *A61M 16/0463* (2013.01); *A61M 2210/1032* (2013.01)

(58) Field of Classification Search
CPC ............ A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; A61B 1/015; A61B 1/04; A61B 1/042; A61B 1/05; A61B 1/051; A61B 1/053
USPC ........ 600/109–113, 121–125, 130–132, 136, 600/156–180
See application file for complete search history.

(56) References Cited

U.S. PATENT DOCUMENTS

| | | | | |
|---|---|---|---|---|
| 7,214,183 | B2 | 5/2007 | Miyake | |
| 7,946,981 | B1* | 5/2011 | Cubb | A61B 1/00052 600/194 |
| 8,128,557 | B2* | 3/2012 | Scholly | A61B 1/128 600/112 |
| 2003/0078476 | A1* | 4/2003 | Hill | A61B 1/00052 600/160 |
| 2004/0054254 | A1 | 3/2004 | Miyake | |
| 2004/0133073 | A1* | 7/2004 | Berci | A61B 1/00188 600/112 |
| 2005/0177024 | A1 | 8/2005 | Mackin | |
| 2007/0049794 | A1* | 3/2007 | Glassenberg | A61B 1/0684 600/109 |
| 2007/0276183 | A1* | 11/2007 | Melder | A61B 1/00128 600/112 |
| 2008/0214896 | A1* | 9/2008 | Krupa | A61B 1/00105 600/136 |
| 2011/0270038 | A1* | 11/2011 | Jiang | A61B 1/267 600/188 |
| 2011/0313245 | A1* | 12/2011 | Scholly | A61B 1/00105 600/104 |
| 2011/0313347 | A1* | 12/2011 | Zocca | A61B 1/00052 604/35 |
| 2012/0078055 | A1* | 3/2012 | Berci | A61B 1/04 600/188 |

FOREIGN PATENT DOCUMENTS

| | | |
|---|---|---|
| JP | 2009-6118 A | 1/2009 |
| WO | 03034905 A2 | 5/2003 |
| WO | 2010/089726 A1 | 8/2010 |

OTHER PUBLICATIONS

Communication dated Nov. 11, 2014 from the Japanese Patent Office in counterpart application No. 2013-543011.
International Search Report for PCT/JP2012/078877 dated Dec. 25, 2012.
Machine Translation of JP 2009-006118, which was cited in the IDS filed on Mar. 24, 2014.
Communication dated Mar. 24, 2015 from the Japanese Patent Office in counterpart application No. 2013-543011.
Communication dated Feb. 27, 2015 from the European Patent Office in counterpart European Application No. 12848366.6.

* cited by examiner

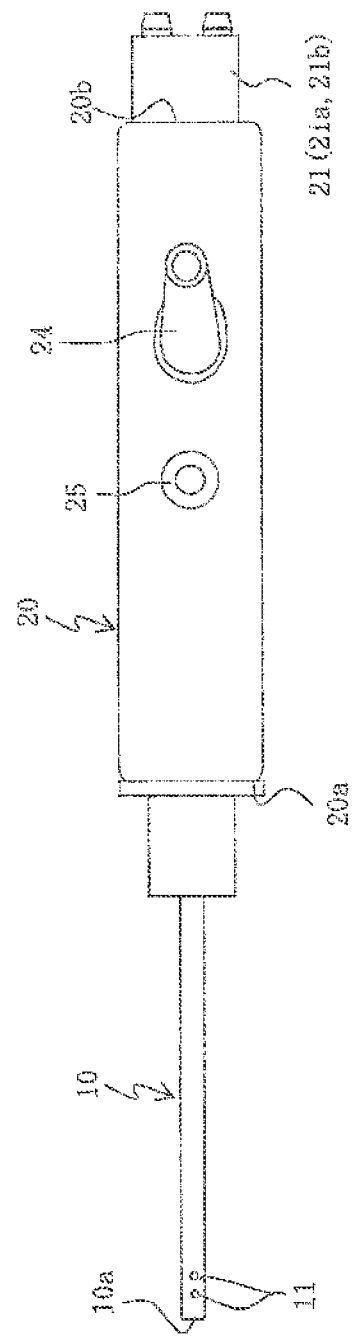

SUCTION CATHETER

CROSS REFERENCE TO RELATED APPLICATIONS

This application is a continuation application based on a PCT Patent Application No. PCT/JP2012/078877, filed Nov. 7, 2012, whose priority is claimed on Japanese Patent Application No. 2011-243784 filed on Nov. 7, 2011, the content of which is hereby incorporated by reference.

BACKGROUND OF THE INVENTION

The present invention relates to an endoscope-attached suction catheter in which attachment and detachment of an imaging unit can be easily carried out.

DESCRIPTION OF THE RELATED ART

In a case where a patient cannot cough up secretion such as phlegm in a trachea or a bronchus, for example, who uses an artificial respirator, removal of the secretion is carried out by use of a suction catheter.

At this time, in order to visually observe an operation portion, removal of the secretion is carried out while using a bronchoscope or an endoscope.

However, since skill is required to simultaneously operate an bronchoscope or an endoscope and a suction catheter, in the case of operation by a caregiver, patient's family, or the like, there is a possibility that removal of the secretion cannot be properly carried out or tracheal mucosa is carelessly damaged by the end of the suction catheter.

Consequently, an endoscope-attached suction catheter has been studied which combines a suction catheter with an endoscope and can carry out suctioning while observing a state of an operation portion with the endoscope (for example, refer to PCT International Publication No. WO2010/089726).

In the endoscope-attached suction catheter, an imaging fiber constituting an endoscope is inserted into a tube of the catheter, and an image propagating through the imaging fiber is image-captured and displayed by an image-capturing-display device that is attachable to and detachable from a control unit of the catheter.

However, in configuration of PCT International Publication No. WO2010/089726, attachment and replacement of the imaging device is carried out at between an optical system of an imaging device and an end face of the imaging fiber.

In the case of the above-described configuration, since the distance between the optical system of the imaging device and the end face of the imaging fiber varies in manufacturing, it is necessary to carry out the focusing of the optical system of the imaging device for each replacement of the imaging device.

SUMMARY OF THE INVENTION

The invention was conceived in view of the above-described circumstances and has an object thereof to provide an endoscope-attached suction catheter which can easily realize attachment and detachment of an imaging unit.

In order to solve the aforementioned problem and achieve the object, a suction catheter of an aspect of the invention adopts the following means.

A suction catheter of an aspect of the invention includes: a catheter main body that includes a suction passage along a longitudinal direction thereof; a control unit that is attached to an end portion of the catheter main body which is opposite to an operation portion; and an imaging unit that is attachable to and detachable from the control unit.

It is preferable that the suction catheter of an aspect of the invention further include an imaging fiber that is arranged inside the catheter main body in a longitudinal direction thereof, passes through the control unit, has an end face that is exposed to an outer surface of the control unit, and propagates an image that is obtained at the operation portion, wherein the imaging unit includes an imaging module that includes an optical system and an imaging device which image-capture the image transmitted to the end face of the imaging fiber, and when the imaging unit is attached to the control unit, the position of the imaging module is fixed so that a distance from the end face of the imaging fiber to the imaging module is constant.

It is preferable that the suction catheter of an aspect of the invention further include: an imaging sensor that is provided at a position of the catheter main body close to the operation portion, and converts an image that is obtained at the operation portion into an electrical signal; and a sensor wiring that is arranged inside the catheter main body in a longitudinal direction thereof, connected to the imaging sensor, and transmits the electrical signal to the imaging unit, wherein the imaging unit includes a signal processing circuit processes the electrical signal that is obtained through the sensor wiring.

It is preferable that the suction catheter of an aspect of the invention further include a light guide that is arranged inside the catheter main body in a longitudinal direction thereof, and propagates illuminating light that illuminates the operation portion.

It is preferable that the suction catheter of an aspect of the invention further include a lighting unit that is provided at the control unit and allows illuminating light to be incident to the light guide.

It is preferable that the suction catheter of an aspect of the invention further include a light source (LED) that is provided at a position of the catheter main body close to the operation portion; and an electric supply line that is arranged inside the catheter main body in a longitudinal direction thereof and supplies electric power to the light source.

In the suction catheter of an aspect of the invention, it is preferable that the imaging unit that includes the imaging module be attachable to and detachable from an upper portion of the control unit.

It is preferable that the suction catheter of an aspect of the invention further include a display unit that is provided at the imaging unit and displays the image captured by the imaging unit.

In the suction catheter of an aspect of the invention, it is preferable that the imaging unit include a removable portion that is attachable to and detachable from the control unit and the imaging module include a pressing portion that allows the removable portion to press against the control unit by generating reactive force in the removable portion.

It is preferable that the suction catheter of an aspect of the invention further include a lighting passage that is provided at the catheter main body and in which the light guide is arranged so as to extend along a longitudinal direction of the catheter main body; and an imaging pathway that is provided at the catheter main body and in which the imaging fiber is arranged so as to extend along a longitudinal direction of the catheter main body.

In the suction catheter of an aspect of the invention, it is preferable that a position of the imaging module be fixed so that a distance from the end face of the imaging fiber to the imaging device is constant.

In the suction catheter of an aspect of the invention, it is preferable that the imaging module include a relay lens and a position of the imaging module be fixed so that the distance from the end face of the imaging fiber to the relay lens is constant.

It is preferable that the suction catheter of an aspect of the invention further include a display unit that is provided at the imaging unit and displays an image corresponding to the electrical signal processed by the signal processing circuit.

Effects of the Invention

In the suction catheter of an aspect of the invention, when the imaging unit is attached to the control unit, the position of the imaging module is fixed so that the distance from the end face of the imaging fiber to the imaging module is fixed.

With this configuration, the distance between the optical system of the imaging unit and the end face of the imaging fiber is stabilized.

Consequently, it is not necessary to carry out the focusing of the optical system of the imaging unit for each replacement of the imaging unit.

As a result, an operator can carry out suctioning and removing of extraneous materials with reference to an image that is displayed on the display unit without performing a complicated operation such as focusing.

Furthermore, in the suction catheter of an aspect of the invention, the imaging sensor obtains an image of the operation portion, and the resultant image is converted into an electrical signal.

The electrical signal is input to the imaging unit through the sensor wiring.

The electrical signal that is input to the imaging unit is processed in the signal processing circuit and is converted into a video signal, and an image is displayed on the display unit.

Consequently, it is not necessary to carry out the focusing of the optical system of the imaging unit for each replacement of the imaging unit.

As a result, an operator can carry out suctioning and removing of extraneous materials with reference to an image that is displayed on the display unit without performing a complicated operation such as focusing.

BRIEF DESCRIPTION OF THE DRAWINGS

FIG. 2B is a top view showing the catheter and the control unit of the first embodiment of the invention.

DETAILED DESCRIPTION OF THE INVENTION

First Embodiment

Hereinafter, a suction catheter of an embodiment of the invention will be described with reference to drawings.

Figure 1:
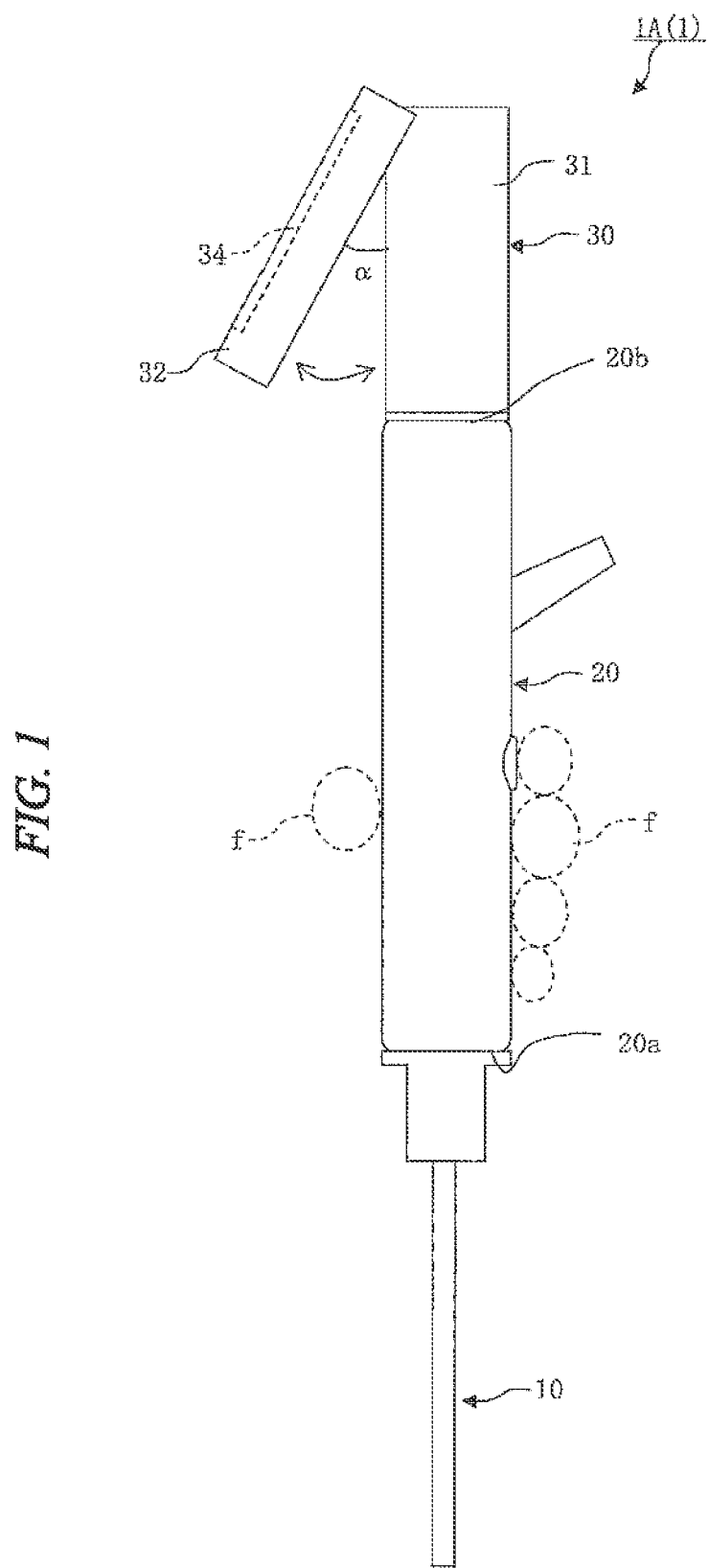
FIG. 1 is a view schematically showing a suction catheter related to a first embodiment of the invention.

FIG. 1 is a view schematically showing a suction catheter related to the first embodiment of the invention.

A suction catheter 1A (1) of the present embodiment is substantially configured to include: a catheter 10 (catheter main body); a control unit 20 connected to the catheter 10; and an imaging unit 30 removably connected to the control unit 20.

The catheter 10 is inserted through one end 20a (first end) of the control unit 20 into the inside thereof.

The control unit 20 is attached to the end portion on the opposite side of a distal end 10a (operation portion) of the catheter 10.

Additionally, the imaging unit 30 is connected to the other end 20b (second end) of the control unit 20.

The suction catheter 1A (1) of the present embodiment is used to suction and remove a patient's deposited matter in their bronchial pathway such as phlegm or secretion, or extraneous materials such as blood (hereinbelow, may simply be referred to as an extraneous material).

Such extraneous material may be the above-described extraneous materials generated in the bronchus or the trachea or may be liquid or the like generated in the buccal capsule or the nasal cavity.

Particularly, a broken line f shown in FIG. 1 is a virtual line representing a user's fingers.

Figure 2A:
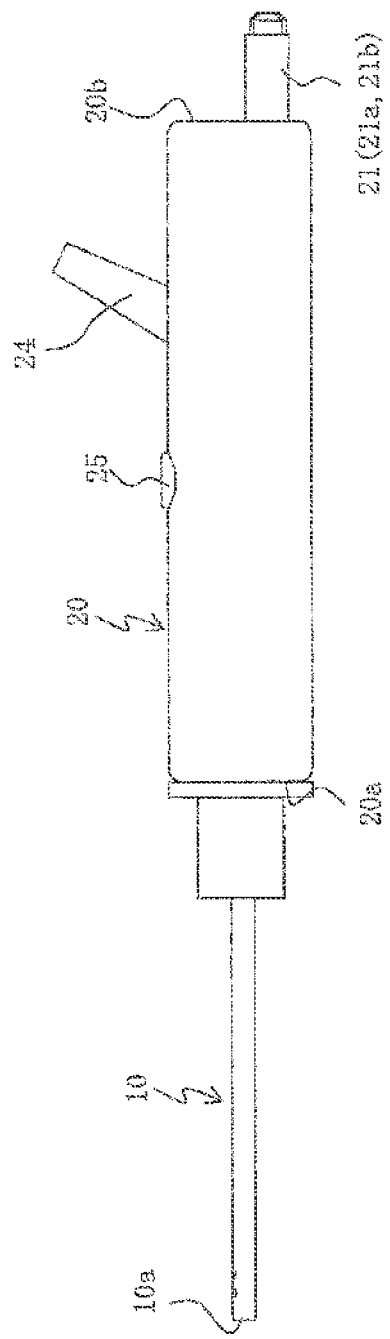
FIG. 2A is a side view showing a catheter and a control unit of the first embodiment of the invention.

FIGS. 2A and 2B are views schematically showing the catheter 10 and the control unit 20 of the suction catheter 1A (1) related to the first embodiment of the invention.

FIG. 2A is a side view showing the catheter 10 and the control unit 20 and FIG. 2B is a top view showing the catheter 10 and the control unit 20.

In the catheter 10, a part of the distal end 10a of the catheter 10 opens (a portion corresponding to a suction passage 12 which will be described later) and extraneous materials are suctioned through the opening.

Moreover, As shown in FIGS. 2A and 2B, the side face of the distal end 10a has a rounded shape.

Because of this, the distal end 10a of the catheter 10 is configured not to damage tracheal mucosa or the like when the catheter 10 is inserted into a patient's trachea.

A plurality of through holes 11 (suctioning hole) which penetrate through the catheter 10 in the thickness direction thereof and have a predetermined size are formed near the distal end 10a of the catheter 10.

The suctioning holes 11 are communicated with the suction passage 12 of the catheter 10 which are described later.

In the present embodiment, two suctioning holes 11 are illustrated as an example; however, the number or a size of the suctioning holes 11, or a distance from the distal end 10a of the catheter 10 thereto is not particularly limited to this.

A configuration of the above-described suctioning holes 11 is suitably adjusted and determined depending on a diameter of the catheter 10 (a size of the suction passage 12 which will be described later), a suction pressure, the degree of viscosity of a main suction-target extraneous material, or the like.

As an example, the distance from the distal end 10a of the catheter 10 to the suctioning holes 11 is approximately 10 mm, and the diameter of the suctioning hole 11 is approximately 1 to 3 mm.

As a result of providing the suctioning holes 11 at the side surface of the catheter 10 in addition to providing openings of the distal end 10a of the catheter 10, suctioning and removing of extraneous materials are carried out in a wide range thereof.

Furthermore, extraneous materials can be suctioned by differently using the opening of the distal end 10a of the catheter 10 or the suctioning holes 11 depending on portions where extraneous materials are present.

A length of the portion of the catheter 10 which extends from the control unit 20 is adjusted so as to correspond to a patient to which the suction catheter 1 of the present embodiment is applied, and the length is approximately 500 mm in the case where, for example, a common adult human uses it.

A diameter of the catheter 10 is not particularly limited to this as long as the diameter is less than or equal to ½ of the internal diameter of a tracheal tube or a tracheostomy tube which are used for intubation and to which the suction catheter 1A of the present embodiment is inserted.

At this time, as a diameter of the catheter 10 becomes thinner (as an internal diameter of the catheter 10 becomes smaller), a length of operation time of removing extraneous materials becomes longer; therefore, a diameter of the catheter 10 is set to a diameter to the extent that an operation time does not become excessively long.

Figure 3:
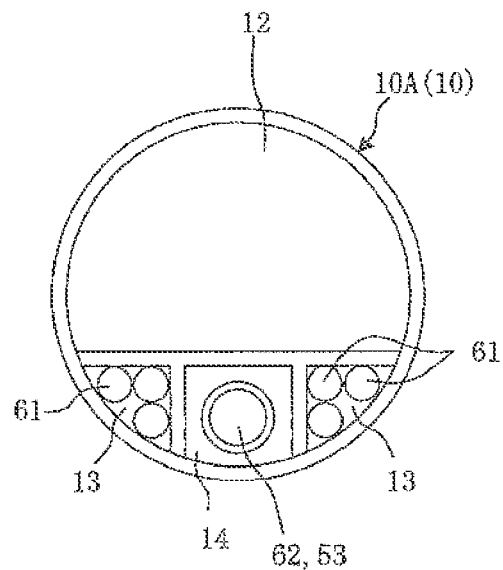
FIG. 3 is a view showing a distal end portion of the catheter of the first embodiment of the invention.

FIG. 3 is a view schematically showing a distal end 10a of the catheter 10A (10) of the present embodiment.

As shown in FIG. 3, the suction passage 12 serving as a removal pathway of an extraneous material that is suctioned through a patient's trachea in the longitudinal direction thereof, a lighting passage 13 in which a light guide 61 illuminating the distal end 10a of the catheter 10 (operation portion) is provided, and an imaging pathway 14 in which an imaging fiber 62 carrying out image-capturing at the distal end 10a of the catheter 10 (image-capturing of an operation portion is carried out) is provided are separately provided in the catheter 10A.

The light guide 61 is arranged along the longitudinal direction of the catheter 10 and propagates illuminating light of the distal end 10a.

Since the passages are individually provided as stated above, stable suctioning and removing of extraneous materials, imaging an operation portion, and illumination can be realized without interfering with each other.

In the catheter 10 of the present embodiment, the imaging pathway 14 is provided below in a height direction in the cross section thereof (a portion that is located at the back side of a patient when insertion into the patient is carried out) and at the center region thereof, and the lighting passage 13 is provided at both sides of the imaging pathway 14.

That is, the imaging pathway 14 and the lighting passage 13 are formed on the opposite side of the position at which the suctioning hole 11 of the catheter 10 is formed.

The catheter 10 in which such suction passage 12, lighting passage 13, and imaging pathway 14 are provided can be manufactured by extrusion molding by use of resins such as natural rubber, synthetic rubber, polyvinyl chloride, or polyurethane, or a material such as silicon.

Thereafter, a suctioning hole 11 or the like having a predetermined size may be formed at a predetermined position by boring or the like.

The catheter 10 is preferably black in color.

For this reason, it is possible to reduce deterioration in a quality of the image that is obtained through the imaging fiber 62.

Additionally, the cross-sectional shape of the catheter 10 is a circle in the present embodiment, however, the shape may be an ellipse or a polygon (here, the corner portions thereof are formed in a rounded shape in order to prevent tracheal mucosa or the like from being damaged when insertion or removal of the catheter 10 and removal of extraneous materials are carried out).

The suction passage 12 is communicated with the aforementioned plurality of suctioning holes 11.

Furthermore, the suction passage 12 opens at the distal end 10a of the catheter 10 and the rear end 10b.

This means that, the suction passage 12 is communicated with a first space 22 of the control unit 20 which will be described later (refer to FIG. 6).

Therefore, the extraneous materials, which are taken through the opening of the distal end 10a of the catheter 10 and the suctioning holes 11, are suctioned to move toward the first space 22 of the control unit 20 through the suction passage 12 located inside the catheter 10, and are discharged from the first space 22 toward the outside of the suction catheter 1.

A plurality of light guides 61 that is constituted of an optical fiber is provided at each lighting passage 13.

Such light guides 61 allows illuminating light 40a emitted from a lighting unit 40 of the imaging unit 30 (refer to FIG. 5) to transmit the distal end 10a of the catheter 10 and illuminates an operation portion.

As a result of providing a plurality of light guides 61, even in the case where one of the light guides 61 is damaged, the other light guides 61 can be used as a backup.

As the light guide 61, for example, it is preferable to use a fine fiber such as one having a diameter of 30 to 70 μm.

As the light guide 61, a plastic optical fiber, a silica-based optical fiber, a multi-component glass fiber, or the like may be adopted.

Such silica-based optical fiber, plastic optical fiber, and multi-component glass fiber may be suitably selected and used depending on the cost of manufacturing or a required light irradiation angle.

In the case of using a silica-based optical fiber, a minimum diameter of an obtained fiber is approximately 70 μm and an irradiation angle thereof is approximately 30 degrees.

Consequently, light irradiation having a wide range cannot be carried out; however, the cost of manufacturing therefor can be reduced as compared with the case of using a multi-component glass fiber.

In the case of using a plastic optical fiber, it is possible to further reduce the cost of manufacturing.

On the other hand, in the case of using a multi-component glass fiber as the light guide 61, a minimum diameter of the fiber is approximately 30 to 50 μm and an irradiation angle of 60 to 120 degrees can be realized.

Because of this, it is possible to illuminate a wide range of an operation portion, and an operation of suctioning and removing extraneous materials is effectively carried out.

An example that three light guides 61 are disposed in each lighting passage 13 is shown in the present embodiment; however, the number of the light guides 61 is not particularly limited to this and may be suitably adjusted depending on the kinds of optical fiber to be used, a diameter of the catheter 10, a required illuminance, or an irradiation angle.

Moreover, a fiber may be suitably selected from the above-described optical fibers depending on where the light guide 61 is disposed, and such fibers may be mixed together and used.

The imaging fiber 62, in which a plurality of optical fibers are collected and fusion-integrated, is disposed in the imaging pathway 14.

The imaging fiber 62 is configured to include: a plurality of cores; and clads that are formed so as to surround such cores.

As a core, for example, silica glass into which $GeO_2$ is doped is adopted.

As a clad, for example, pure silica glass or pure silica glass into which fluorine or the like is doped is adopted.

A distance between the cores adjacent to each other is, for example, approximately 3 μm.

The distance between the cores is suitably determined based on a refractive index difference between the core and the clad.

Where, for example, a refractive index difference of core/clad is 2 to 5%, preferably 3.5 to 4%, a distance of 3 μm between the cores can be achieved.

At this time, due to reduction in the distance between the cores, a larger number of optical fibers can be collected.

As a result, a clean and wide-range video picture is obtained.

The number of optical fibers (number of pixels) to be collected is preferably, for example, a thousand to hundred thousand.

If the number of optical fibers (number of pixels) is less than a thousand, a clean image may not be obtained.

On the other hand, if the number of optical fibers (number of pixels) exceeds hundred thousand, the fine imaging fiber 62 cannot be obtained.

As the imaging fiber 62, for example, a graded index type optical fiber can be adopted.

As stated above, since the imaging fiber 62 is provided in the suction catheter 1 of the present embodiment, a video picture at the distal end 10a of the catheter 10 (operation portion) is obtained.

As a result, an operation of removing extraneous materials is carried out with reference to the video picture.

For this reason, an advanced technique is not necessary, and the operation of removing extraneous materials is simply carried out.

An object lens 53 is disposed at an end of the imaging fiber 62 (the distal end side 10a of the catheter 10).

At this time, the end of the imaging fiber 62 to which a sleeve is adhesively attached serves as a polished surface, and the object lens 53 is attached to the polished surface.

The object lens 53 is not particularly limited and a SELFOC lens (registered trademark) is preferable therefor.

As such SELFOC lens, a SELFOC lens having, for example, a working distance (WD) of approximately 15 mm is used.

Figure 4A:
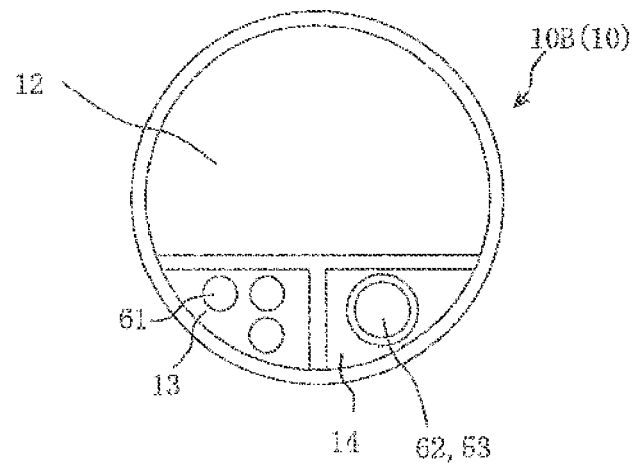
FIG. 4A is a view showing a modified example of the catheter of the first embodiment of the invention and is a view illustrating the distal end portion of the catheter.
Figure 4B:
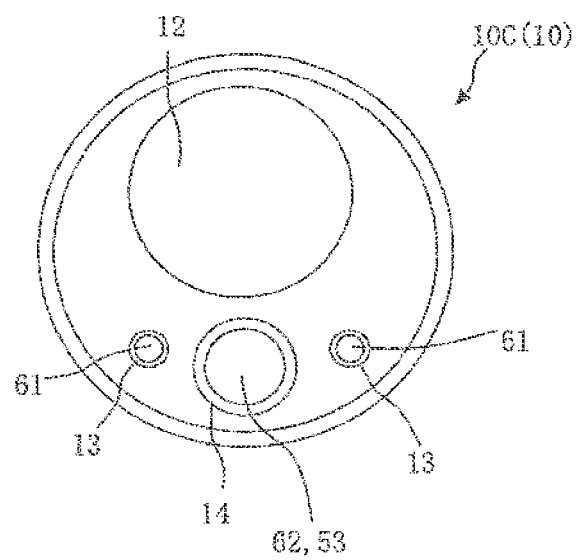
FIG. 4B is a view showing a modified example of the catheter of the first embodiment of the invention and is a view illustrating the distal end portion of the catheter.
Figure 4C:
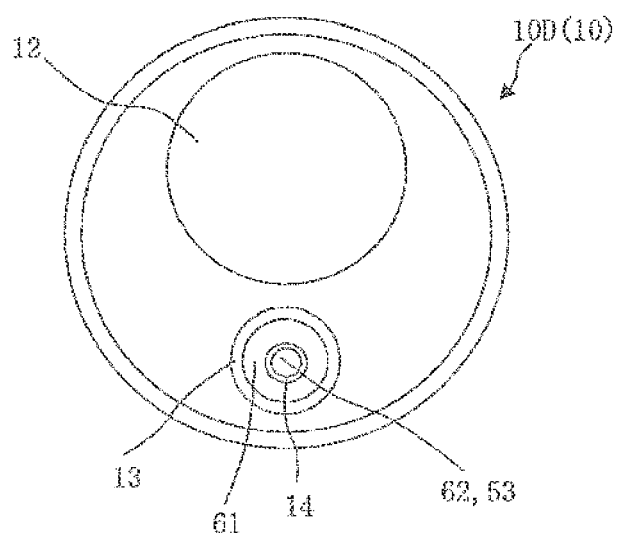
FIG. 4C is a view showing a modified example of the catheter of the first embodiment of the invention and is a view illustrating the distal end portion of the catheter.

FIGS. 4A to 4C are views showing modified examples of the catheter 10.

In a modified example of a catheter 10B (10) shown in FIG. 4A, the lower portion in a height direction in the cross section thereof (a portion that is located at the back side of a patient when insertion into the patient is carried out) is separated into two spaces, one of the spaces forms the imaging pathway 14, and the other of the spaces forms the lighting passage 13.

In a modified example of a catheter 10C (10) shown in FIG. 4B, the suction passage 12, the lighting passage 13, and the imaging pathway 14 are formed in a circular shape in cross section.

In a modified example of a catheter 10D (10) shown in FIG. 4C, the suction passage 12 is formed in a circular shape in cross section.

Furthermore, the lighting passage 13 and the imaging pathway 14 are concentrically formed in a circular shape in cross section so as to surround the imaging pathway 14.

Even in cases where the catheter 10B, 10C, or 10D having the above-described configuration is used, the same effect as in the above-mentioned case is obtained.

Figure 6:
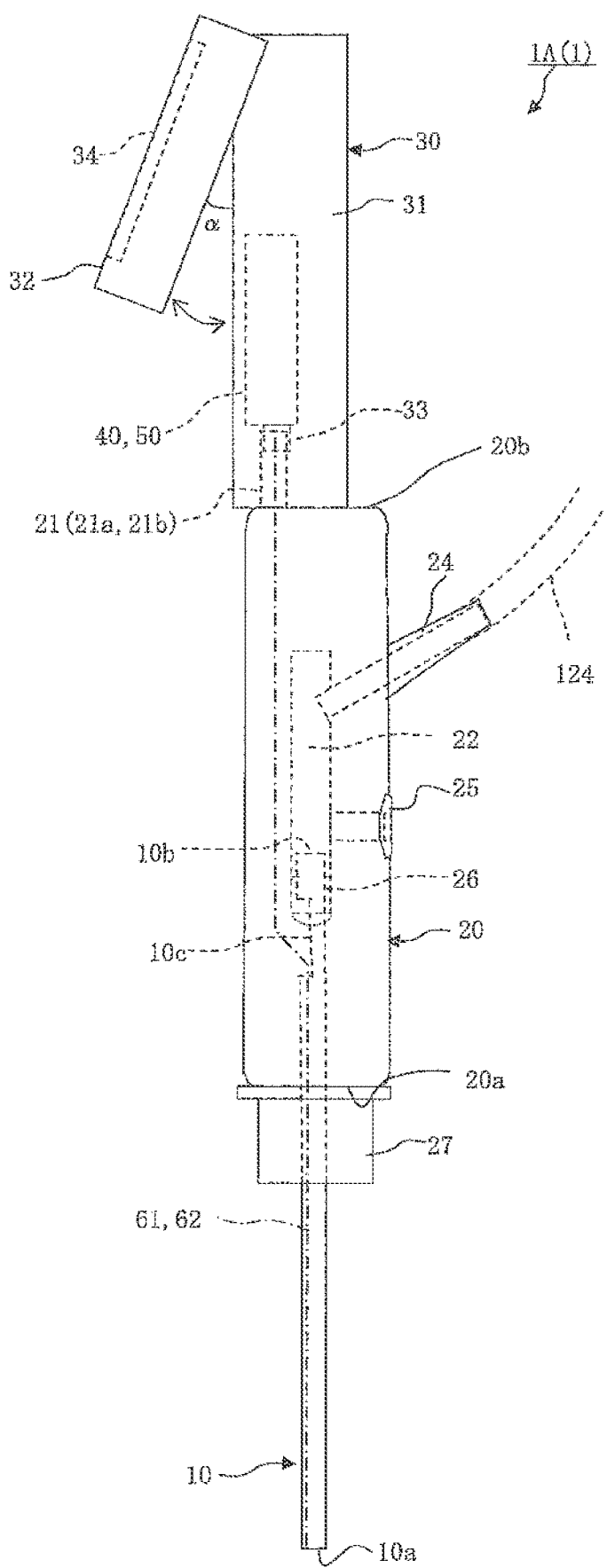
FIG. 6 is a view showing the suction catheter of the first embodiment of the invention and schematically showing main components inside the imaging unit and the control unit.

A cut-off portion 10c that exposes the lighting passage 13 and the imaging pathway 14 to the outside of the catheter 10 is formed at the other end side 10b of the catheter 10 that is disposed inside the control unit 20 (refer to FIG. 6).

The light guide 61 that is disposed at the lighting passage 13 and the imaging fiber 62 that is disposed at the imaging pathway 14 are extracted from the inside of the catheter 10 through the cut-off portion 10c, and are optically connected to the imaging unit 30 that is connected to the control unit 20.

The light guide 61 and the imaging fiber 62 are bended and disposed in the control unit 20.

At this time, the catheter 10 is configured so that an optical loss due to excessive bending of the light guide 61 and the imaging fiber 62 does not occur.

As shown in FIG. 6, the first space 22 that is communicated with the suction passage 12 of the catheter 10 is formed in the control unit 20.

Furthermore, a socket 24 that has a hollow shape and is connected to a suction device (not shown in the figure) via a tube 124 and an adjustment port 25 that is communicated with an outside space of the control unit 20 are communicated with the first space 22.

As shown in FIGS. 2A, 2B, 5, and 6, a removable portion 21 that is connectable to the imaging unit 30 is formed at the other end 20b (the portion at which the catheter 10 is not disposed) of the control unit 20.

A cross-sectional shape of the control unit 20 may be a circle or the shape other than a circle.

The cross-sectional configuration of the control unit 20 is not particularly limited as long as the control unit 20 is fitted to a user's hand and an operation such as rotation can be carried out without discomfort when a user operates and holds the control unit 20 with their hand.

The configuration may be, for example, an ellipse or a polygon such as a tetragon or a hexagon.

The rear end 10b of the catheter 10 is disposed in the first space 22, and the suction passage 12 of the catheter 10 is communicated with the first space 22.

A resin 26 is disposed between an inner wall of the first space 22 and a side surface of the catheter 10.

By means of this structure, the first space 22 is airtightly and adhesively attached to the side surface of the catheter 10.

As described above, the socket 24 having a hollow shape and the adjustment port 25 are formed at the first space 22.

The socket 24 is connected to a suction device (not shown in the figure) via the tube 124.

The suction device generates a negative pressure inside a suction passage of the extraneous materials (the suction passage 12 of the catheter 10, the first space 22 and the socket 24 of the control unit 20), and carries out suctioning and removing of the extraneous materials.

The suction device is not particularly limited, a diaphragm type suction device may be adopted, and a tube-pump type suction device may be adopted.

A pressure during suction is suitably determined depending on an individual patient or the symptom thereof, for example, 5 Pa to 15 kPa.

As the adjustment port 25 is sealed by user's finger f in a state where the suction device is activated (refer to FIG. 1), an internal pressure of the suction passage in addition to the first space 22 becomes a negative pressure.

In this case, patient's extraneous materials are suctioned through at least one of the suctioning holes 11 and the opening of the distal end 10a of the catheter 10 which are disposed at the distal end side 10a of the catheter 10.

The sucked extraneous materials are collected by a foreign material gathering device provided at the suction device through the suction passage 12, the first space 22, the socket 24, and the tube 124.

At this time, a suction pressure can be adjusted by adequately changing the degree of sealing of the adjustment port 25.

For this reason, suctioning and removing of the extraneous materials can be carried out at an appropriate suction pressure depending on the extraneous materials to be suctioned.

Since the degrees of viscosity of extraneous materials are different as needed depending on the kinds thereof or patient's conditions, an optimal suction pressure varies.

Conventionally, since extraneous materials to be suctioned cannot be visually checked, it is difficult to perform the suctioning them while instantaneously changing a suction pressure depending on each extraneous material.

According to the suction catheter 1A of the present embodiment, since a step of suctioning and removing the kinds of extraneous material to be suctioned is carried out based on the video picture that is obtained through the imaging fiber 62, a suction pressure is adequately changed by simultaneously adjusting an opening angle of the adjustment port 25 depending on the degree of viscosity of an extraneous material, and suctioning of the extraneous materials is carried out.

As a result, suctioning and removing of the extraneous materials having various viscosities can be effectively realized in a shorter amount of time than ever before.

In the present embodiment, the control unit 20 is connected to the catheter 10 via a connector 27 that is disposed at the end 20a of the control unit 20.

In this case, the connector 27 is fixed to the catheter 10 using an adhesive.

Similarly, the connector 27 is connected to the control unit 20 using an adhesive.

By means of this structure, force that is applied to the catheter 10 during operation of removing extraneous materials is inhibited from being only applied to the resin 26 that adhesively attaches the catheter 10 to the first space 22.

As a result, an operation of removing extraneous materials is reliably carried out without applying excessive force to the resin 26 that adhesively attaches the catheter 10 to the first space 22, without failing airtightness between the catheter 10 and the first space 22 during an operation, and without deterioration in a suction pressure.

Additionally, the suction catheter 1A is easily manufactured by use of the connector 27.

A method of manufacturing the suction catheter 1A of the present embodiment will be described.

After the control unit 20 is manufactured by, for example, extrusion molding, the light guide 61 and the imaging fiber 62 which are extracted from the cut-off portion 10c are disposed at a predetermined position in the control unit 20.

Thereafter, the other end 10b of the catheter 10 is disposed in the first space 22, the resin 26 is applied thereon and cured.

Subsequently, the catheter 10 can be fixed to the control unit 20 by use of the connector 27.

Accordingly, even in the case of manufacturing a suction catheter 1A using catheters 10 having diameters different from each other, it is possible to manufacture a suction catheter in accordance with the intended use by only changing the diameter of the portion into which the catheter 10 of the connector 27 is inserted.

A terminal connector 21a of the light guide 61 and a terminal connector 21b of the imaging fiber 62 are formed at the removable portion 21.

The light guide 61 is joined to the terminal connector 21a with an adhesive, and the fiber end face of the light guide 61 is polished.

Similarly, the imaging fiber 62 is adhesively attached to the terminal connector 21b, and the fiber end face (the end face that is exposed at the external surface of the control unit) of the imaging fiber 62 is polished.

Such light guide 61 and imaging fiber 62 are optically connected to the imaging unit 30 through the terminal connectors 21a and 21b.

Particularly, connection terminals 33a and 33b which are connected to such terminal connectors 21a and 21b, respectively, are formed at the removable portion 21 of the imaging unit 30 and the control unit 20.

Figure 5:
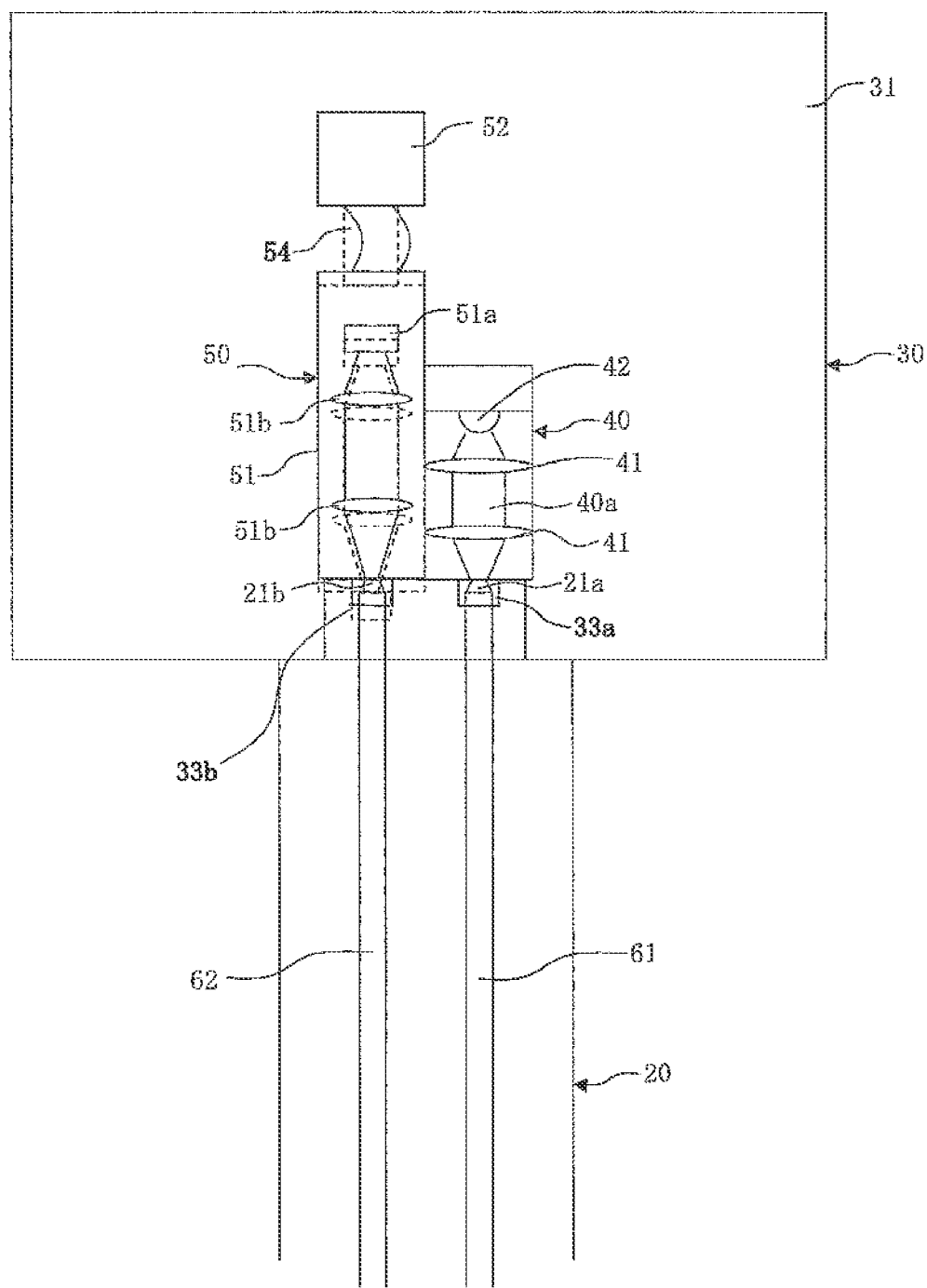
FIG. 5 is a view showing an example of an imaging unit the first embodiment of the invention.

As shown in FIGS. 5 and 6, the imaging unit 30 that is used in the suction catheter 1A of the present embodiment is substantially configured to include: a housing 31; a display unit 32 that is disposed at one face of the housing 31; and the lighting unit 40 and the imaging module 50 which are disposed inside the housing 31.

FIG. 5 is a view showing a relevant part of the lighting unit 40 and the imaging module 50 in the imaging unit 30.

As shown in FIG. 6, the display unit 32 is located on the opposite side of the surface on which a connector 24 of the control unit 20 or an adjustment hole 25 are formed when the imaging unit 30 is connected to the control unit 20.

The display unit 32 is disposed at the housing 31 via a hinge, a ball joint, or the like, and the display unit 32 is variable with respect to the housing 31 as shown in FIG. 6 (an angle α formed between the display unit 32 and the housing 31 varies in the range of 0 to 90 degrees).

As a result of adjusting the angle α, a screen 34 of the display unit 32 is inhibited from being hardly viewed due to reflection of light or the like, suctioning and removing of the extraneous materials can be carried out in accordance with a video picture displayed on the display unit 32.

An anti-reflective film or the like may be provided at the screen 34 of the display unit 32.

As shown in FIG. 5, the lighting unit 40 is substantially configured to include a plurality of lenses 41 and a light source 42.

Light emitted from the light source 42 is collected in and incident to the light guide 61 through the lenses 41.

The number of the lenses 41, the configuration thereof, or the material thereof is not particularly limited as long as light emitted from the light source 42 can be collected in the light guide 61.

The light source 42 is not particularly limited as long as illuminating light can be realized to the extent that an user can be in visual contact with extraneous materials and patient's tracheal mucosa and identify them when an operation portion is illuminated; a high-luminance white LED (Light Emitting Diode) having a high level of visibility for the operation portion is preferable.

The imaging module 50 is substantially configured by an optical system 51 including an imaging device (imaging element) 51a such as a CCD camera and a plurality of lenses 51b.

Additionally, the imaging module 50 is connected to a printed board 52, that performs control of the imaging device 51a, with flexible flat cable (FFC) 54 interposed therebetween.

An image that is transmitted through the imaging fiber 62 is focused onto the imaging device 51a, serves as an image signal, and is output from the imaging device 51a.

The image signal is transmitted to the printed board 52 through the FFC 54 and finally displayed on the display unit 32 as an image (video picture).

Moreover, as shown in FIG. 5, the imaging unit 30 that is provided with the imaging module 50 including the imaging device 51a is detachably provided above the control unit 20.

The above-described configuration of the suction catheter is completely different from a configuration of a conventional suction catheter which has an imaging sensor provided in a catheter main body and a circuit unit provided in an imaging unit.

The imaging module 50 includes a pressing portion that causes reaction force to occur in the removable portion 21 and presses the removable portion 21 against the control unit 20 (refer to FIGS. 7A to 7D).

Specifically, the imaging module 50 is pressed downward (the control unit side 20) by an elastic member (pressing portion) such as a spring, and the movement thereof can be realized inside the housing 31.

Because of this, the imaging device 51a is connected to the printed board 52 with the FFC 54 having a high level of flexibility interposed therebetween.

In particular, pressing of the imaging module 50 against the control unit 20 means that force (reactive force) acts with respect to the imaging module 50 as a result of the restorative force generated by the elastic member, and the imaging module 50 is pressed against the removable portion 21 (connection terminal 33b).

Accordingly, when the imaging unit 30 is attached to the control unit 20, the position of the imaging module 50 is fixed so that a distance from the end face of the imaging fiber 62 to the imaging module 50 is constant.

As shown in FIG. 5, when the control unit 20 is connected to the imaging unit 30, the terminal connectors 21a and 21b (the removable portion 21) of the light guide 61 and the imaging fiber 62 which are formed in the control unit 20 come into contact with the connection terminals 33 (33a, 33b) of the imaging unit 30, respectively.

At this time, as shown in FIG. 5, the terminal connector 21b of the imaging fiber 62 upwardly pushes the optical systems 51.

Since the printed board 52 is fixed to the imaging unit 30, the FFC 54 is in a state of being bent.

Moreover, in FIG. 5, the imaging module 50 and the FFC 54 which are indicated by a dotted line represent a state before they moves to the upper part of the paperface.

In the present embodiment, the imaging unit 30 is designed so that light emitted from the light source 42 is collected in the light guide 61 and light transmitted through the imaging fiber 62 is focused onto the imaging device 51a when the terminal connectors 21a and 21b of the control unit 20 come into contact with the connection terminals 33 (33a, 33b) of the imaging unit 30.

Particularly, as a result of causing the terminal connector 21*b* to come into contact with the connection terminal 33*b* and to press up the imaging module 50, the imaging module 50 moves to the position at which light transmitted through the imaging fiber 62 is incident to the imaging module 50.

In this way, connection between the imaging unit 30 and the control unit 20 is completed.

As a result, an operation of adjusting the light focus is not necessary, and an operator can carry out suctioning and removing of extraneous materials with reference to an image that is displayed on the display unit 32 without performing a complicated operation such as focusing.

Next, a configuration of the pressing portion to which the imaging module 50 is provided will be specifically described with reference to FIG. 7A.

Figure 7A:
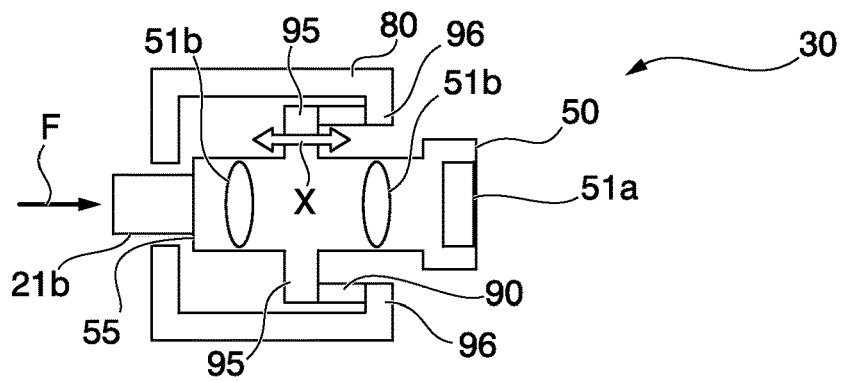
FIG. 7A is a view showing a pressing portion constituting the suction catheter of the first embodiment of the invention and is a cross-sectional view schematically showing a main component of an imaging module.

FIG. 7A is a view showing a pressing portion constituting the suction catheter of the present embodiment and is a cross-sectional view schematically showing a main component of an imaging module.

A frame 80, a pressing portion 90, and the imaging module 50 are provided inside the imaging unit 30.

Protruding portions 96 that protrude toward the inside of the frame 80 are provided at the frame 80.

The imaging module 50 configures a lens frame.

A plurality of lenses 51*b* arranged inside the lens frame so as to form an optical system.

The imaging module 50 has a contacting face 55 and a projected portion 95.

In addition, the imaging device 51*a* is provided on the opposite side of the contacting face 55.

The projected portion 95 faces the protruding portions 96.

Moreover, FIG. 7A shows a state where the terminal connector 21*b* is in contact with the contacting face 55 by the action of the force represented by reference letter F; when the control unit 20 is connected to the imaging unit 30, the terminal connector 21*b* of the imaging fiber 62 comes into contact with the contacting face 55.

The pressing portion 90 is an elastic member constituted of, for example, a coil spring, a plate spring, or the like, and is provided between the protruding portion 96 of the frame 80 and the projected portion 95 of the imaging module 50.

The pressing portion 90 is extendable in the direction represented by reference letter X.

In the imaging module 50 having the above-described configuration, when the control unit 20 is connected to the imaging unit 30, the force F is applied to the imaging module 50, the terminal connector 21*b* of the imaging fiber 62 comes into contact with the contacting face 55, the pressing portion 90 is compressed, and the imaging module 50 moves toward the right direction in FIG. 7A.

For this reason, the position of the imaging module 50 is fixed so that a distance from the end face of the imaging fiber 62 (the terminal connector 21*b*) to the imaging device 51*a* of the imaging module 50 is constant.

That is, the force F and the reactive force acting on the pressing portion 90 (restorative force, force acting in a direction in which the pressing portion 90 extends) are balanced in a state where the pressing portion 90 is compressed, the imaging module 50 and the terminal connector 21*b* are static, and the distance between the terminal connector 21*b* and the imaging device 51*a* is maintained constant.

Because of this, it is possible to use the suction catheter 1A (1) in a state where the control unit 20 is connected to the imaging unit 30 without carrying out a complicated focusing or the like.

Additionally, when the control unit 20 is removed from the imaging unit 30, the imaging module 50 moves toward the left direction in FIG. 7A as a result of the restorative force generated by the pressing portion 90, the terminal connector 21*b* is removed from the imaging module 50.

<Modified Example 1 of Pressing Portion>

Figure 7B:
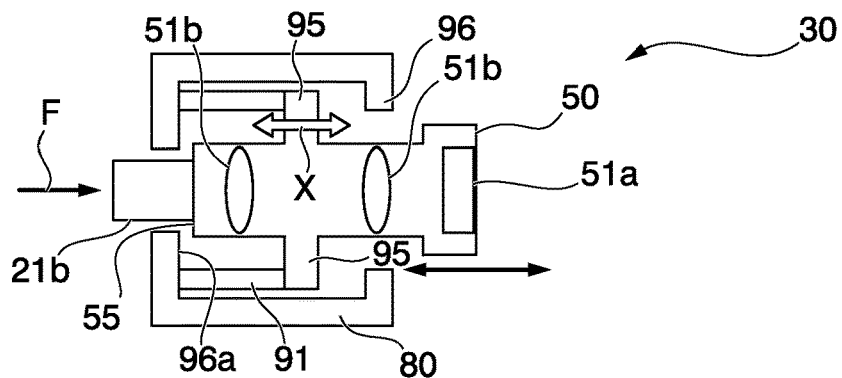
FIG. 7B is a view showing a modified example 1 of a pressing portion constituting the suction catheter of the first embodiment of the invention and is a cross-sectional view schematically showing a main component of the imaging module.

FIG. 7B is a view showing a pressing portion constituting the suction catheter of the present embodiment and is a cross-sectional view schematically showing a main component of an imaging module.

In FIG. 7B, identical symbols are used for the elements which are identical to those of FIG. 7A, and the explanations thereof are omitted or simplified here.

A frame 80, a pressing portion 91, and the imaging module 50 are provided inside the imaging unit 30.

A compressive face 96*a* is provided at the frame 80 and at the position close to the terminal connector 21*b*.

The projected portion 95 of the imaging module 50 faces the compressive face 96*a*.

Moreover, as similar to FIG. 7A, FIG. 7B shows a state where the terminal connector 21*b* is in contact with the contacting face 55 by the action of the force represented by reference letter F.

The pressing portion 91 is provided between the compressive face 96*a* of the frame 80 and the projected portion 95 of the imaging module 50.

In the imaging module 50 having the above-described configuration, when the control unit 20 is connected to the imaging unit 30, the force F is applied to the imaging module 50, and the pressing portion 91 extends.

For this reason, the position of the imaging module 50 is fixed so that a distance from the end face of the imaging fiber 62 (the terminal connector 21*b*) to the imaging device 51*a* of the imaging module 50 is constant.

That is, the force F and the reactive force acting on the pressing portion 91 (restorative force, force acting in a direction in which the pressing portion 91 extends) are balanced in a state where the pressing portion 91 expands, the imaging module 50 and the terminal connector 21*b* are static, and the distance between the terminal connector 21*b* and the imaging device 51*a* is maintained constant.

Consequently, the same effect as that in the above-described case is obtained.

<Modified Example 2 of Pressing Portion>

Figure 7C:
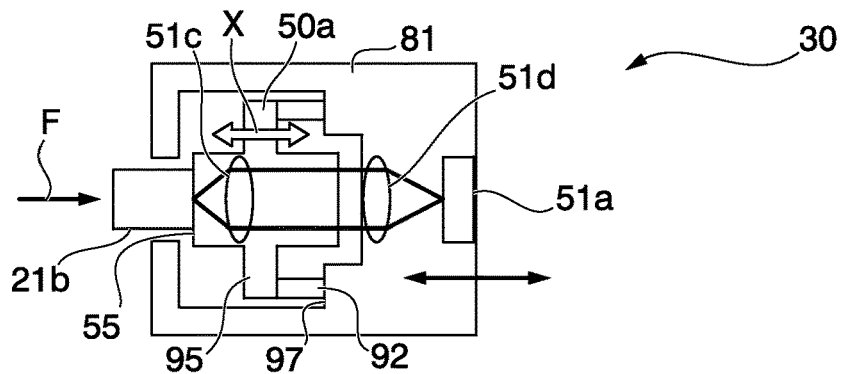
FIG. 7C is a view showing a modified example 2 of a pressing portion constituting the suction catheter of the first embodiment of the invention and is a cross-sectional view schematically showing a main component of the imaging module.

FIGS. 7A and 7B illustrates the structure in which the imaging module 50 including the lens 51*b* and the imaging device 51*a* moves by being pressed by the terminal connector 21*b*; in contrast, FIG. 7C shows a structure in which a lens system constituting the imaging module 50 is a relay lens barrel.

In FIG. 7C, the imaging module 50 is pushed by the terminal connector 21*b*, and a front lens system barrel only moves.

FIG. 7C is a view showing a pressing portion constituting the suction catheter of the present embodiment and is a cross-sectional view schematically showing a main component of an imaging module.

A frame 81, a pressing portion 92, and an imaging module 50*a* are provided inside the imaging unit 30.

A compressive face 97, a frame lens 51*d*, and the imaging device 51*a* are provided at the frame 81.

In the configuration, an optical image obtained from the imaging module 50*a* enters the imaging device 51*a* through the frame lens 51*d*.

The imaging module 50*a* constitutes a lens frame.

The front lens system barrel including a relay lens 51*c* is provided inside the lens frame.

The imaging module 50*a* includes the contacting face 55 and the projected portion 95.

The projected portion 95 faces the compressive face 97.

Moreover, FIG. 7C shows a state where the terminal connector 21*b* is in contact with the contacting face 55 by the action of the force represented by reference letter F; when the control unit 20 is connected to the imaging unit 30, the terminal connector 21*b* of the imaging fiber 62 comes into contact with the contacting face 55.

The pressing portion 92 is an elastic member constituted of, for example, a coil spring, a plate spring, or the like, and is provided between the compressive face 97 of the frame 81 and the projected portion 95 of the imaging module 50*a*.

The pressing portion 92 is extendable in the direction represented by reference letter X.

In the imaging module 50*a* having the above-described configuration, when the control unit 20 is connected to the imaging unit 30, the force F is applied to the imaging module 50*a*, the terminal connector 21*b* of the imaging fiber 62 comes into contact with the contacting face 55, the pressing portion 92 is compressed, and the imaging module 50*a* moves toward the right direction in FIG. 7C.

For this reason, the position of the imaging module 50*a* is fixed so that a distance from the end face of the imaging fiber 62 (the terminal connector 21*b*) to the relay lens 51*c* (front lens system barrel) is constant.

That is, the force F and the reactive force acting on the pressing portion 92 (restorative force, force acting in a direction in which the pressing portion 92 extends) are balanced in a state where the pressing portion 92 is compressed, the imaging module 50*a* and the terminal connector 21*b* are static, and the distance between the terminal connector 21*b* and the relay lens 51*c* is maintained constant.

Because of this, it is possible to use the suction catheter 1A (1) in a state where the control unit 20 is connected to the imaging unit 30 without carrying out a complicated focusing or the like.

Additionally, when the control unit 20 is removed from the imaging unit 30, the imaging module 50*a* moves toward the left direction in FIG. 7C as a result of the restorative force generated by the pressing portion 92, the terminal connector 21*b* is removed from the imaging module 50*a*.

<Modified Example 3 of Pressing Portion>

Figure 7D:
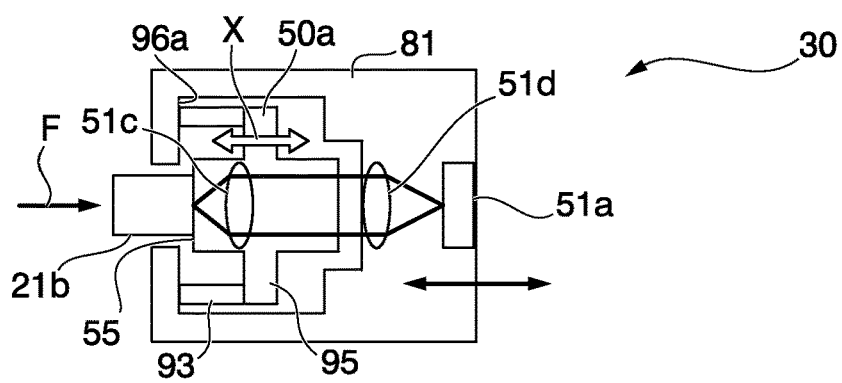
FIG. 7D is a view showing a modified example 3 of a pressing portion constituting the suction catheter of the first embodiment of the invention and is a cross-sectional view schematically showing a main component of the imaging module.

FIG. 7D is a view showing a pressing portion constituting the suction catheter of the present embodiment and is a cross-sectional view schematically showing a main component of an imaging module.

In FIG. 7D, identical symbols are used for the elements which are identical to those of FIG. 7C, and the explanations thereof are omitted or simplified here.

A frame 81, a pressing portion 93, and the imaging module 50*a* are provided inside the imaging unit 30.

A compressive face 96*a* is provided at the frame 81 and at the position close to the terminal connector 21*b*.

The projected portion 95 of the imaging module 50*a* faces the compressive face 96*a*.

Moreover, as similar to FIG. 7C, FIG. 7D shows a state where the terminal connector 21*b* is in contact with the contacting face 55 by the action of the force represented by reference letter F.

The pressing portion 93 is provided between the compressive face 96*a* of the frame 81 and the projected portion 95 of the imaging module 50*a*.

In the imaging module 50*a* having the above-described configuration, when the control unit 20 is connected to the imaging unit 30, the force F is applied to the imaging module 50*a*, and the pressing portion 93 extends.

For this reason, the position of the imaging module 50*a* is fixed so that a distance from the end face of the imaging fiber 62 (the terminal connector 21*b*) to the relay lens 51*c* (front lens system barrel) is constant.

That is, the force F and the reactive force acting on the pressing portion 93 (restorative force, force acting in a direction in which the pressing portion 93 extends) are balanced in a state where the pressing portion 93 expands, the imaging module 50*a* and the terminal connector 21*b* are static, and the distance between the terminal connector 21*b* and the relay lens 51*c* is maintained constant.

Consequently, the same effect as that in the above-described case is obtained.

According to the suction catheter 1A of the present embodiment, suctioning and removing of the extraneous materials are carried out while adjusting the opening angle of the adjustment port 25 with their forefinger based on an image displayed on the screen 34 of the display unit 32 of the imaging unit 30 that is disposed at a user's hand.

In the case where the image is arranged at the position apart from a suction catheter, in order to operate the suction catheter disposed at hand with reference to the video picture, it is necessary to get used thereto.

As the screen 34 of the display unit 32 of the imaging unit 30 is disposed at hand such as the present embodiment, a further instinctive operation of operation of the suction catheter 1A can be realized, and it is possible to efficiently perform suctioning and removing of the extraneous materials.

In the present embodiment, the catheter 10 may be bended toward the suctioning hole 11.

As the catheter 10 is bended, the opening of the distal end 10*a* of the catheter 10 and the suctioning holes 11 is easily come close to extraneous materials that adheres to the inside of a patient's trachea, and suctioning of the extraneous materials becomes easy.

Moreover, a degree of hardness of the catheter 10 may vary in the longitudinal direction thereof.

Of the catheter 10 extending toward the outside of the control unit 20, the portion that has a length corresponding to approximately ⅓ of the length from the distal end 10*a* of the catheter 10 is softer than the remaining portion of the catheter 10 which has a length of approximately ⅔ thereof.

Therefore, when an operation of rotating the suction catheter 1 is carried out inside the patient's trachea, the portion 10*d* quickly moves in accordance with the rotation operation, and the opening of the distal end 10*a* of the catheter 10 and the suctioning holes 11 is made to move to a desired position.

Accordingly, operation of removing extraneous materials can be effectively carried out, and operation time can be reduced.

Specifically, it is preferable that the distal end 10*a* of the catheter 10 has flexibility.

Because of this, when the catheter 10 is inserted into the trachea, the tracheal mucosa is less easily damaged even where the distal end 10*a* comes into contact with the tracheal mucosa.

A method of changing a degree of hardness of the catheter 10 is not particularly limited as long as the catheter 10 can be manufactured so as to have a desired degree of hardness.

For example, a method of manufacturing the catheter 10 to change a thickness thereof depending on the position thereof, a method of manufacturing the catheter to change a material therefor depending on the portion thereof, or a method of coating the portion (location) that has a length corresponding to approximately ⅓ of the length from the distal end 10a of the catheter 10 and thereby making the portion harder than the other portions, or the like is adopted.

At this time, a degree of hardness of the catheter 10 may be made hard in a stepwise manner or a linear manner.

As mentioned above, according to the suction catheter 1A of the present embodiment, insertion of the catheter 10 can be carried out with reference to the video picture obtained by the imaging fiber 62.

For this reason, since it is possible to simultaneously grasp the position of the distal end 10a of the catheter 10, damage to patient's tracheal mucosa or contraction thereof which is due to unnecessary and excessive intrusion of the catheter 10 into patient's trachea does not occur.

In addition, since suctioning and removing of the extraneous materials from patient's trachea can be carried out with reference to the image, removal of extraneous materials can be carried out while visually checking a state of suctioning of the extraneous materials.

Thus, even in cases where degrees of viscosity are different depending on extraneous materials, a suction pressure can be suitably changed depending on a target extraneous material by adjusting an opening angle of the adjustment port 25 provided at the control unit 20, and removal of extraneous materials can be efficiently carried out.

Accordingly, time required for treatment can be shortened and the patient's burden is thereby reduced.

Furthermore, since the imaging module 50 is pressed toward the direction of the connection of the control unit 20 thereto in the imaging unit 30, the imaging module 50 moves to the position at which light transmitted through the imaging fiber 62 is incident to the imaging module 50 when being connected to the control unit 20.

Consequently, the user can connect the control unit 20 to the imaging unit 30 in a simple and suitable state without carrying out a complicated focusing or the like.

In particular, since the imaging unit 30 is disposed at the control unit 20 in the present embodiment, the user can instinctively operate the suction catheter 1A with reference to the image at their hand.

Second Embodiment

Figure 8:
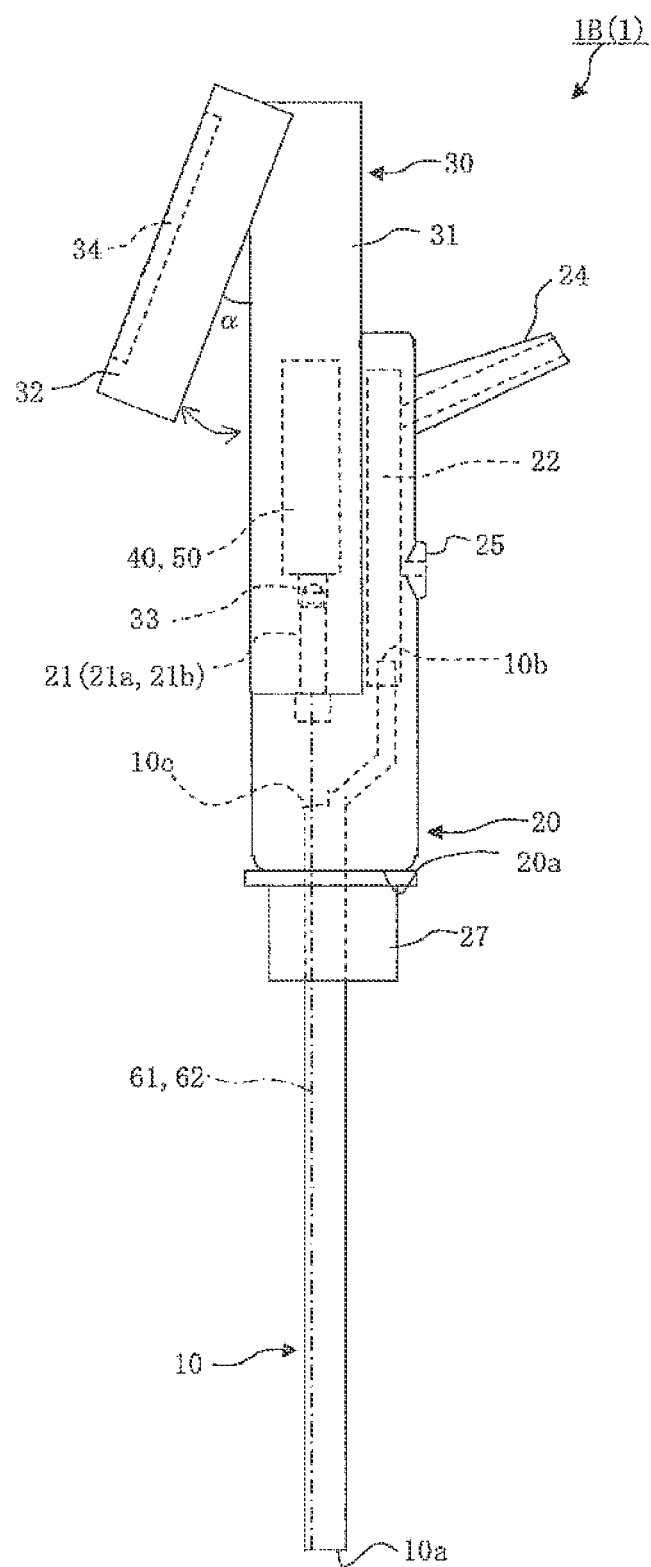
FIG. 8 is a view schematically showing a suction catheter related to a second embodiment of the invention and schematically showing main components inside an imaging unit and a control unit.

FIG. 8 is a view schematically showing a suction catheter 1B (1) related to the second embodiment of the invention.

The suction catheter 1B of the present embodiment is different from the suction catheter 1A of the first embodiment in that a part of the control unit 20 and a part of the imaging unit 30 are disposed so as to overlap each other.

In the suction catheter 1 of the second embodiment of the invention, a user holds the control unit 20 near the first space 22 with their hand.

In the suction catheter 1A of the above-mentioned first embodiment, the lighting unit 40 and the imaging module 50 which are weighty are located above a user's hand.

On the other hand, parts of the lighting unit 40 and the imaging module 50 overlap a part of the first space 22 in the present embodiment.

Furthermore, the control unit 20 is connected to the imaging unit 30 so that the removable portion between the control unit 20 and the imaging unit 30 is located between the end 20a of the control unit and the adjustment port 25 or the socket 24.

As a result of adopting this configuration, when a user grasps the suction catheter 1B, the lighting unit 40 or the imaging module 50 which is weighty is disposed near a user's hand.

Because of this, a balance is stable when the suction catheter 1B is held, and handleability and operability are improved.

Moreover, since a load to be applied to a user's hand in a working state decreases, lessening of fatigue is realized.

As a result, suctioning and removing of the extraneous materials can be effectively carried out in a short amount of time.

In addition, in the above-mentioned first and second embodiments, the configuration is illustrated in which the lighting unit 40 provided with the light source 42 serving as a white LED is provided in the imaging unit 30, but the invention is not limited to this configuration.

The light source 42 may be provided at the position close to the operation portion of the catheter 10.

In this case, an LED is used as the light source 42, an electric supply line that supplies electric power to the LED is disposed inside the catheter 10 along the longitudinal direction thereof.

Furthermore, an object lens may be provided at the LED.

Third Embodiment

In the above-mentioned first and second embodiments, the suction catheter using an imaging fiber is described.

The invention is not limited to a suction catheter using an imaging fiber.

In the third embodiment of the invention, a suction catheter using an imaging sensor instead of an imaging fiber, which converts an image obtained at an operation portion into an electrical signal, will be described.

Particularly, in the third embodiment, identical symbols are used for the elements which are identical to those of the above-mentioned first and second embodiments, and the explanations thereof are omitted or simplified here.

Figure 9A:
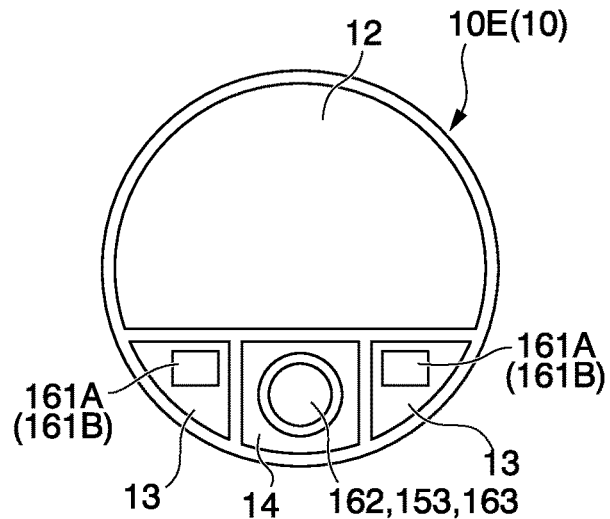
FIG. 9A is a view showing a catheter of a third embodiment of the invention and is a view illustrating a distal end portion of the catheter.

FIG. 9A is a view schematically showing the distal end 10a of the catheter 10E (10) of the present embodiment.

As shown in FIG. 9A, the suction passage 12 serving as a removal pathway of an extraneous material that is suctioned through a patient's trachea in the longitudinal direction thereof, two lighting passages 13 in which a light guide 161A illuminating the distal end 10a (operation portion) of the catheter 10E (10) or a LED 161B (Light Emitting Diode) is provided, and an imaging pathway 14 in which a CMOS imaging sensor 162 (Complementary Metal-Oxide Semiconductor) that carries out image-capturing at the distal end 10a of the catheter 10 (carrying out image-capturing of an operation portion) is provided are separately provided in the catheter 10E.

Here, in the case of using the LED 161B, an electric supply line that supplies electric power to the LED 161B is disposed inside the catheter 10E (10) along the longitudinal direction thereof.

Here, the CMOS imaging sensor 162 corresponds to the imaging sensor of the invention.

The CMOS imaging sensor 162 is provided at the position close to the operation portion of the catheter 10E (catheter main body), and a video picture that is obtained at an operation portion is converted into electrical signals.

Furthermore, an object lens 153 is provided at the CMOS imaging sensor 162.

Similarly, an object lens is provided on the light guide 161A or the LED 161B.

Particularly, the light guide 161A corresponds to the light guide 61 that is described in the above-mentioned first and second embodiments.

Moreover, a sensor wiring 163 is arranged inside the catheter 10E (10) in the longitudinal direction thereof.

The sensor wiring 163 is connected to the CMOS imaging sensor 162 and transmits an electrical signal output from the CMOS imaging sensor 162 to an imaging unit 130 (described hereinbelow).

In other cases, a CCD camera (Charge Coupled Device) may be used instead of the CMOS imaging sensor 162.

Figure 9B:
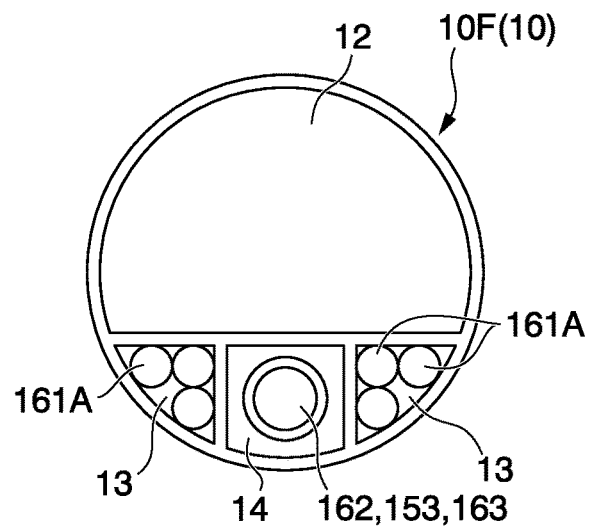
FIG. 9B is a view showing a modified example 1 of the catheter of the third embodiment of the invention and is a view illustrating a distal end portion of the catheter.

FIG. 9B is a view schematically showing the distal end 10a of the catheter 10F (10) of the present embodiment and illustrating a modified example 1 of the catheter.

In the modified example 1 of the catheter, the light guide 161A is provided at each of two lighting passages 13.

The CMOS imaging sensor 162, the object lens 153, and the sensor wiring 163, which are describe above, are provided in the imaging pathway 14.

Figure 9C:
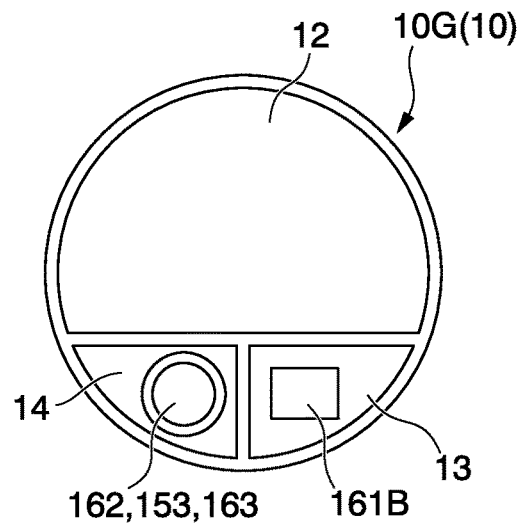
FIG. 9C is a view showing a modified example 2 of the catheter of the third embodiment of the invention and is a view illustrating a distal end portion of the catheter.

FIG. 9C is a view schematically showing the distal end 10a of the catheter 10G (10) of the present embodiment and illustrating a modified example 2 of the catheter.

In the modified example 2 of the catheter, one lighting passage 13 is provided and the lighting passage 13 is arranged parallel to the imaging pathway 14.

The CMOS imaging sensor 162, the object lens 153, and the sensor wiring 163, which are described above, are provided in the imaging pathway 14.

The LED 161B and an object lens that is provided at the LED 161B are arranged in the lighting passage 13.

In FIGS. 9A to 9C shown in above, the CMOS imaging sensor 162 is used as an imaging sensor, the invention is not limited to this configuration, a CIS device (Contact Image Sensor) serving as one of imaging devices may be used instead of the CMOS imaging sensor 162.

Next, a structure in which the sensor wiring 163 is connected to the imaging unit 130 with an electric connector interposed therebetween and a structure of the imaging unit 130 will be described with reference to FIGS. 10A to 12B.

Figure 10A:
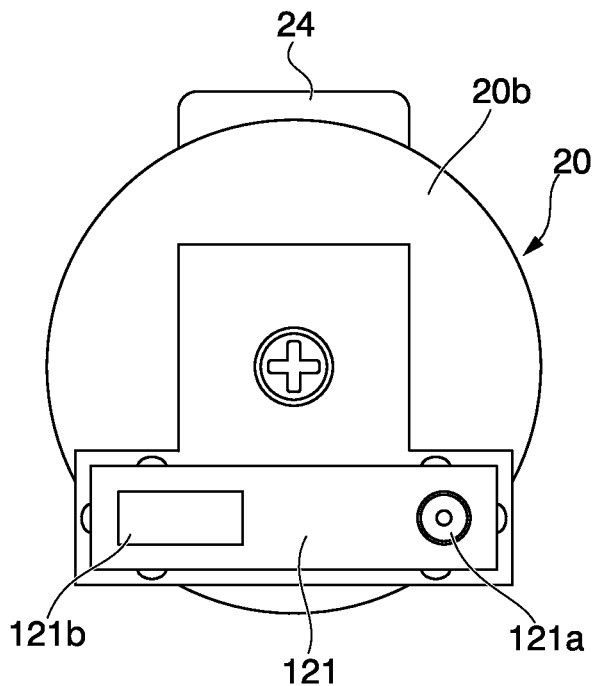
FIG. 10A is a top view showing a control unit that constituting the suction catheter of the third embodiment of the invention and is a view illustrating an electric connector.

FIG. 10A is a top view showing a control unit that constituting the suction catheter and is a view illustrating an electric connector.

As shown in FIG. 10A, a removable portion 121 is provided at the other end 20b of the control unit 20.

A terminal connector 121a that is to be connected to the light guide 161A or the LED 161B and an electric connector 121b that is to be connected to the CMOS imaging sensor 162 are provided at the removable portion 121.

When the control unit 20 is connected to the imaging unit 130, the electric connector 121b is electrically connected to the imaging unit 130.

Figure 10B:
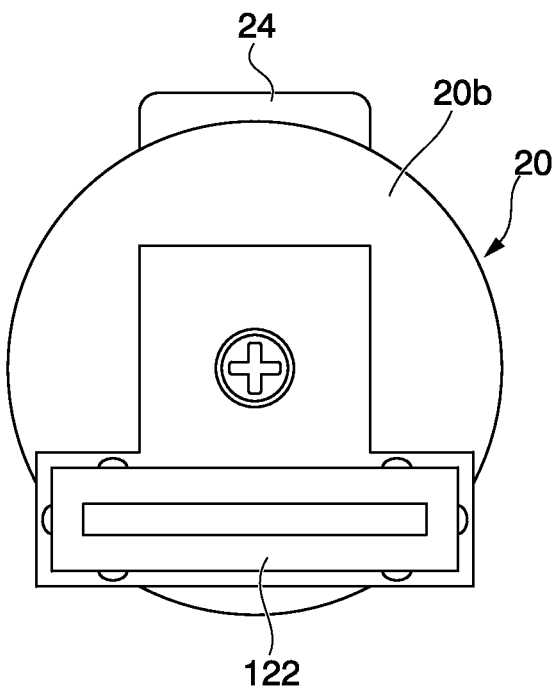
FIG. 10B is a view showing a modified example of the catheter of the third embodiment of the invention and is a view illustrating an electric connector.

In other cases, an electric connector 122 shown in FIG. 10B may be adopted as a modified example of the removable portion 121.

A signal line that is to be connected to a CIS device and an electric power line (electric supply line) that supplies electric power to the LED are provided at the electric connector 122.

Figure 11A:
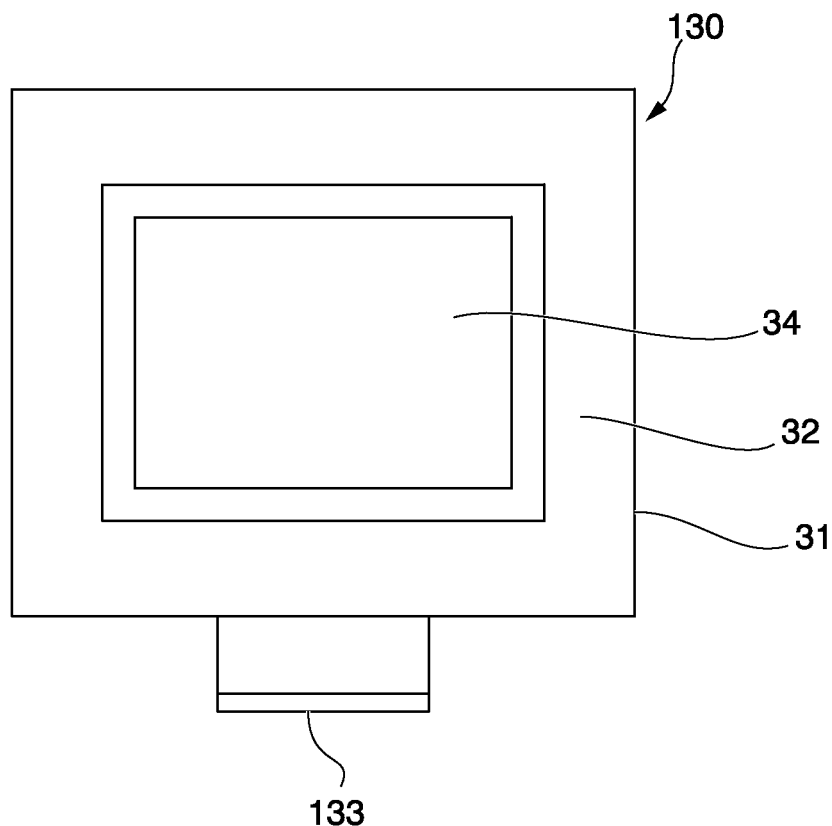
FIG. 11A is a front view showing an imaging unit of the third embodiment of the invention.

FIG. 11A is a front view showing the imaging unit 130 of the third embodiment of the invention.

The imaging unit 130 is constituted of the housing 31, the display unit 32, the screen 34, and a connection terminal 133.

The display unit 32 displays the video picture in accordance with the electrical signal processed by an interface board 131 that is described below.

Figure 11B:
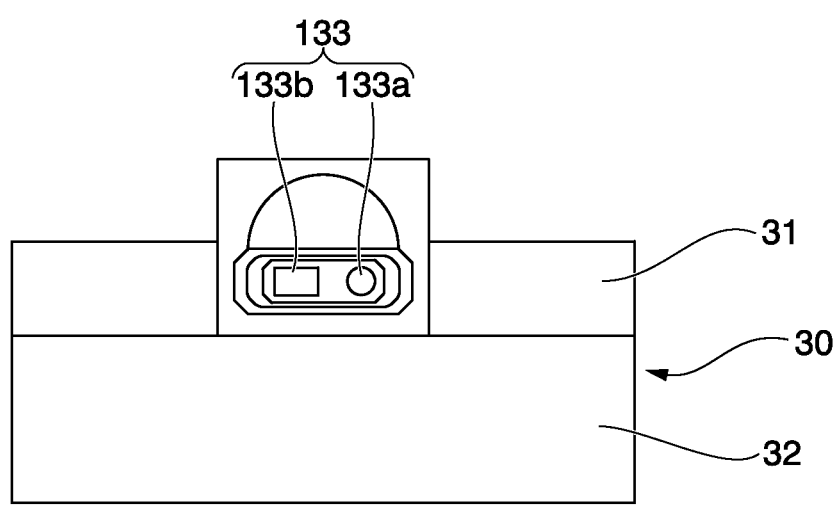
FIG. 11B is a bottom view showing the imaging unit of the third embodiment of the invention.

FIG. 11B is a bottom view showing the imaging unit 130.

As shown in FIG. 11B, the connection terminal 133 is provided with: connection terminal 133b that is to be connected to the electric connector 121b; and a connection terminal 133a that is to be connected to the terminal connector 121a.

For this reason, when the control unit 20 is connected to the imaging unit 130, the CMOS imaging sensor 162 is electrically connected to the imaging unit 130 through the connection terminal 133b.

In addition, in the structure in which the LED 161B is used, the LED 161B is electrically connected to the imaging unit 130 through the connection terminal 133a.

Moreover, in the structure in which the light guide 161A is used, an optical system that is provided inside the imaging unit 130 is optically connected to the light guide 161A through the connection terminal 133a.

Figure 12A:
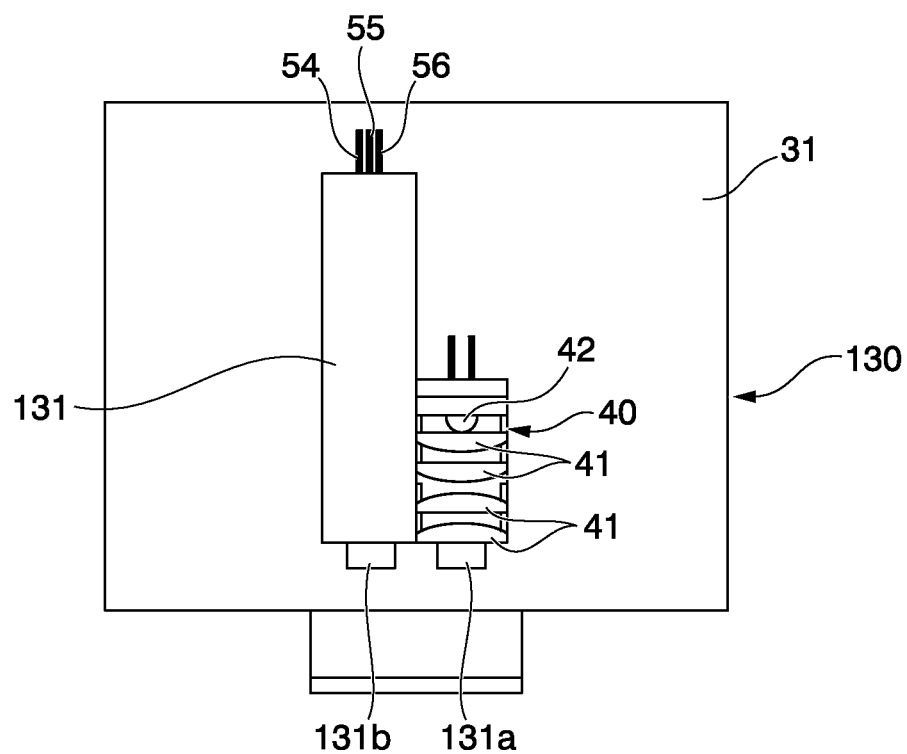
FIG. 12A is a schematic diagram showing the imaging unit of the third embodiment of the invention.

FIG. 12A is a schematic diagram showing the imaging unit 130 of the third embodiment of the invention.

The imaging unit 130 includes: the interface board 131 (signal processing circuit) that processes an electrical signal obtained through the sensor wiring 163; and the lighting unit 40 which is explained in FIG. 5.

The interface board 131 converts, into a video signal, the electrical signal that is output from the CMOS imaging sensor 162, passes through the sensor wiring 163, the electric connector 121b, and the connection terminal 133b, and reaches the interface board 131.

Additionally, various wirings such as a GND wiring 154, a voltage cable 155, a video signal wiring 156 (image output signal wiring) are electrically connected to the interface board 131.

Figure 12B:
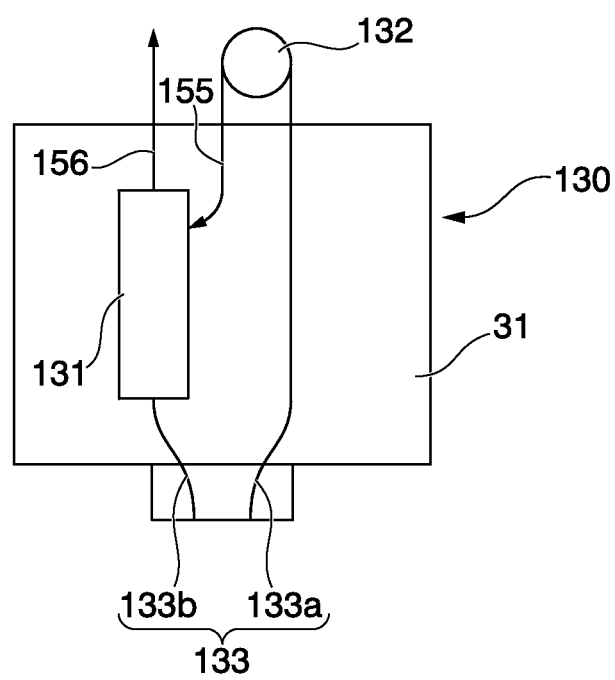
FIG. 12B is a circuit block diagram illustrating the imaging unit of the third embodiment of the invention.

FIG. 12B is a circuit block diagram illustrating the imaging unit 130 of the third embodiment of the invention.

A power supply 132 such as a battery is connected to the imaging unit 130.

The power supply 132 supplies electric power to the interface board 131 through the voltage cable 155.

The video signal wiring 156 that is connected to the interface board 131 is connected to a terminal that is provided at the outside of the imaging unit 130, and a video signal can be output to external monitor through the terminal.

In the aforementioned third embodiment, the CMOS imaging sensor 162 obtains an image of the operation portion, and the resultant image is converted into an electrical signal.

The electrical signal is input to the imaging unit 130 through the sensor wiring 163 and the connection terminal 133.

The electrical signal that is input to the imaging unit 130 is processed in the interface board 131 and thereby converted into a video signal, and the video picture is displayed on the display unit 32.

Consequently, it is not necessary to carry out the focusing of the optical system of the imaging unit for each replacement of the imaging unit.

As a result, an operator can carry out suctioning and removing of extraneous materials with reference to an image that is displayed on the display unit without performing a complicated operation such as focusing.

Fourth Embodiment

Subsequently, the fourth embodiment of the invention will be described.

In the present embodiment, a CIS device (imaging sensor) is used instead of the CMOS imaging sensor 162.

Particularly, in the fourth embodiment, identical symbols are used for the elements which are identical to those of the above-mentioned first, second, and third embodiments, and the explanations thereof are omitted or simplified here.

Figure 13A:
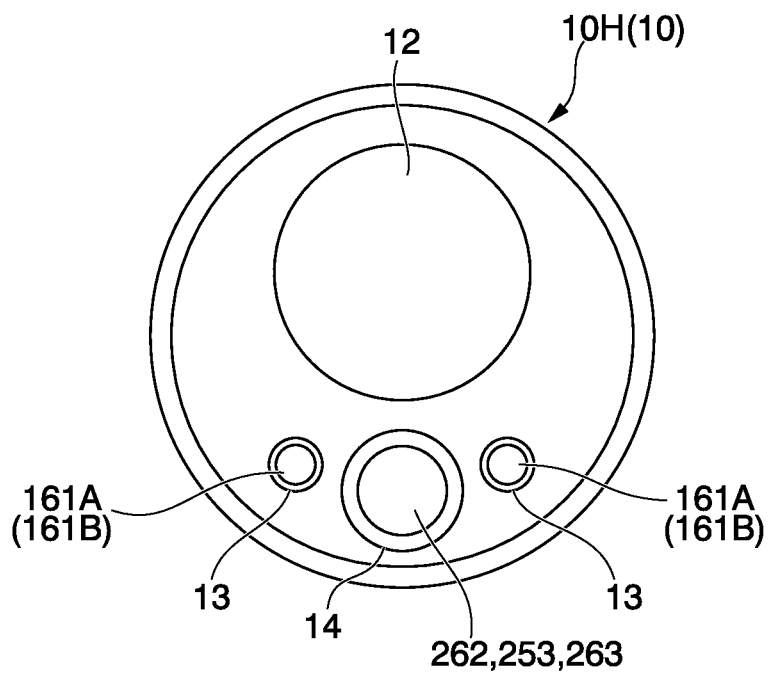
FIG. 13A is a view showing a catheter of a fourth embodiment of the invention and is a view illustrating a distal end portion of the catheter.

FIG. 13A is a view schematically showing the distal end 10a of the catheter 10H (10) of the present embodiment.

In a modified example of a catheter 10H (10) shown in FIG. 13A, the suction passage 12, the lighting passage 13, and the imaging pathway 14 are formed in a circular shape in cross section.

The light guide 161A or the LED 161B which illuminates the distal end 10a (operation portion) of the catheter 10H (10) is provided at two lighting passages 13.

A CIS device 262 is provided at the imaging pathway 14.

An object lens 253 is provided at the CIS device 262.

Additionally, a sensor wiring 263 is provided inside the imaging pathway 14 in the direction in which the catheter extends.

The sensor wiring 263 is connected to the CIS device 262 and transmits a signal that is output from the CIS device 262 to an imaging unit.

Figure 13B:
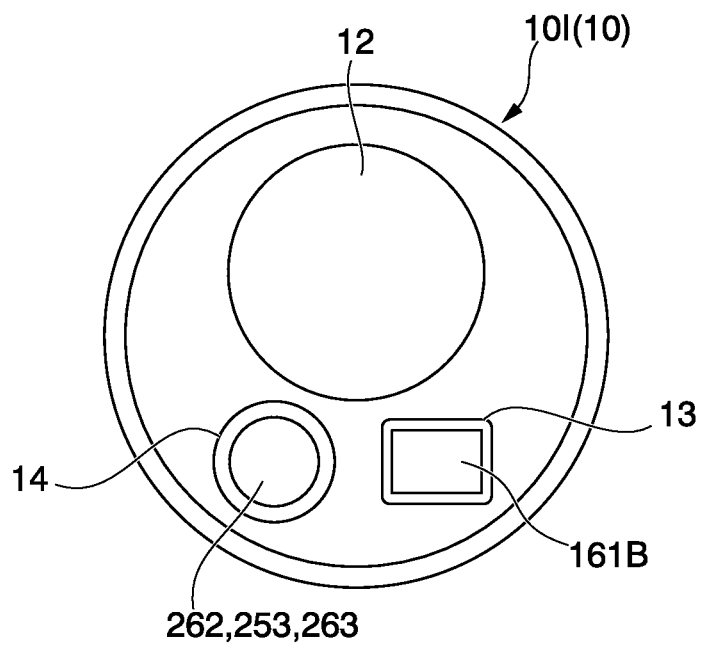
FIG. 13B is a view showing a modified example 1 of the catheter of the fourth embodiment of the invention and is a view illustrating a distal end portion of the catheter.

FIG. 13B is a view schematically showing the distal end 10a of the catheter 10I (10) of the present embodiment and illustrating a modified example 1 of the catheter.

In the modified example 1 of the catheter, one lighting passage 13 is provided, and the lighting passage 13 is arranged parallel to the imaging pathway 14.

In the imaging pathway 14, the CIS device 262, the object lens 253, and the sensor wiring 263 which are described above are provided.

The LED 161B and an object lens that is provided at the LED 161B are arranged in the lighting passage 13.

Figure 13C:
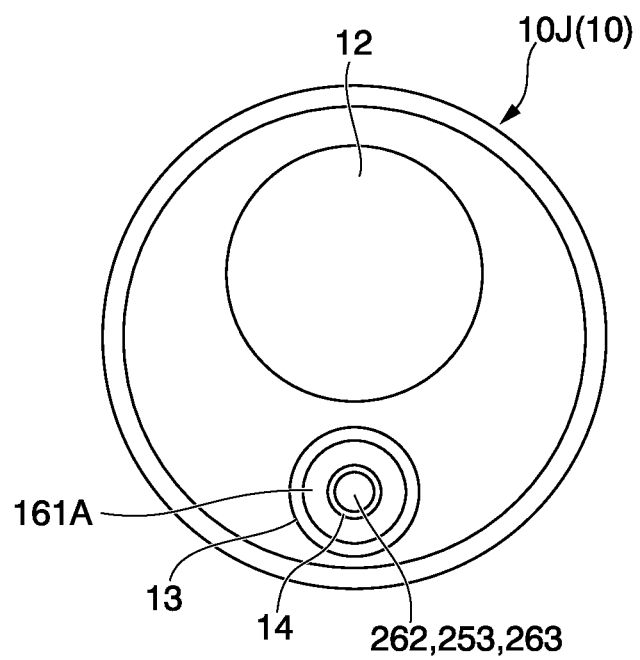
FIG. 13C is a view showing a modified example 2 of the catheter of the fourth embodiment of the invention and is a view illustrating a distal end portion of the catheter.

FIG. 13C is a view schematically showing the distal end 10a of the catheter 10J (10) of the present embodiment and illustrating a modified example 2 of the catheter.

In the modified example 2 of the catheter, the lighting passage 13 and the imaging pathway 14 are coaxially arranged.

In the imaging pathway 14, the CIS device 262, the object lens 253, and the sensor wiring 263 which are described above are provided.

The light guide 161A and an object lens that is provided at the object lens 153 are arranged in the lighting passage 13.

Figure 13D:
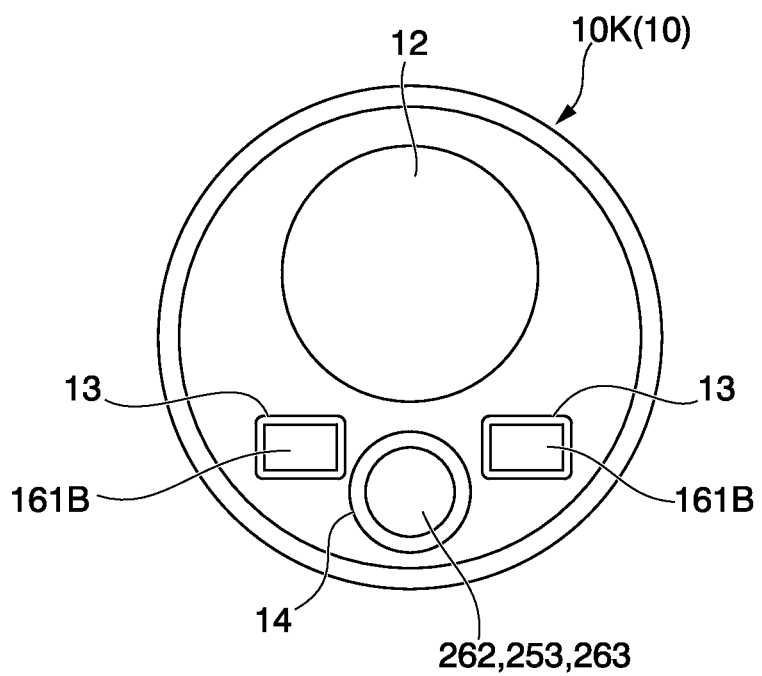
FIG. 13D is a view showing a modified example 3 of the catheter of the fourth embodiment of the invention and is a view illustrating a distal end portion of the catheter.

FIG. 13D is a view schematically showing the distal end 10a of the catheter 10l (10) of the present embodiment and illustrating a modified example 3 of the catheter.

In the modified example 3 of the catheter, two lighting passages 13 are provided, and the two lighting passages 13 is arranged parallel to the imaging pathway 14.

In the imaging pathway 14, the CIS device 262, the object lens 253, and the sensor wiring 263 which are described above are provided.

The LED 161B and an object lens that is provided at the LED 161B are arranged in each of the two lighting passages 13.

In the above-mentioned fourth embodiment, the same effect as that in the third embodiment is obtained.

Fifth Embodiment

Figure 14A:
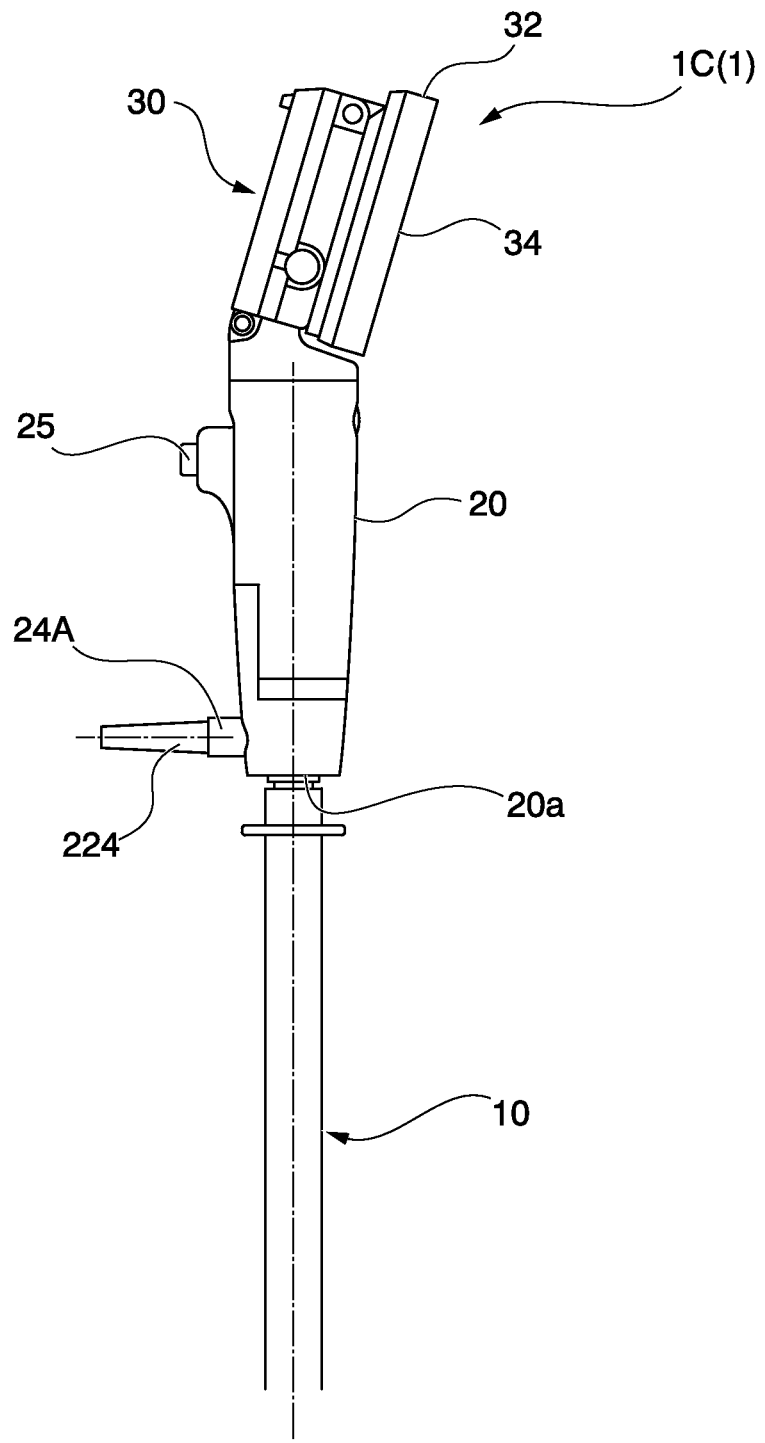
FIG. 14A is a view schematically showing a suction catheter related to a fifth embodiment of the invention and illustrating a structure in which a control unit is connected to an imaging unit.
Figure 14B:
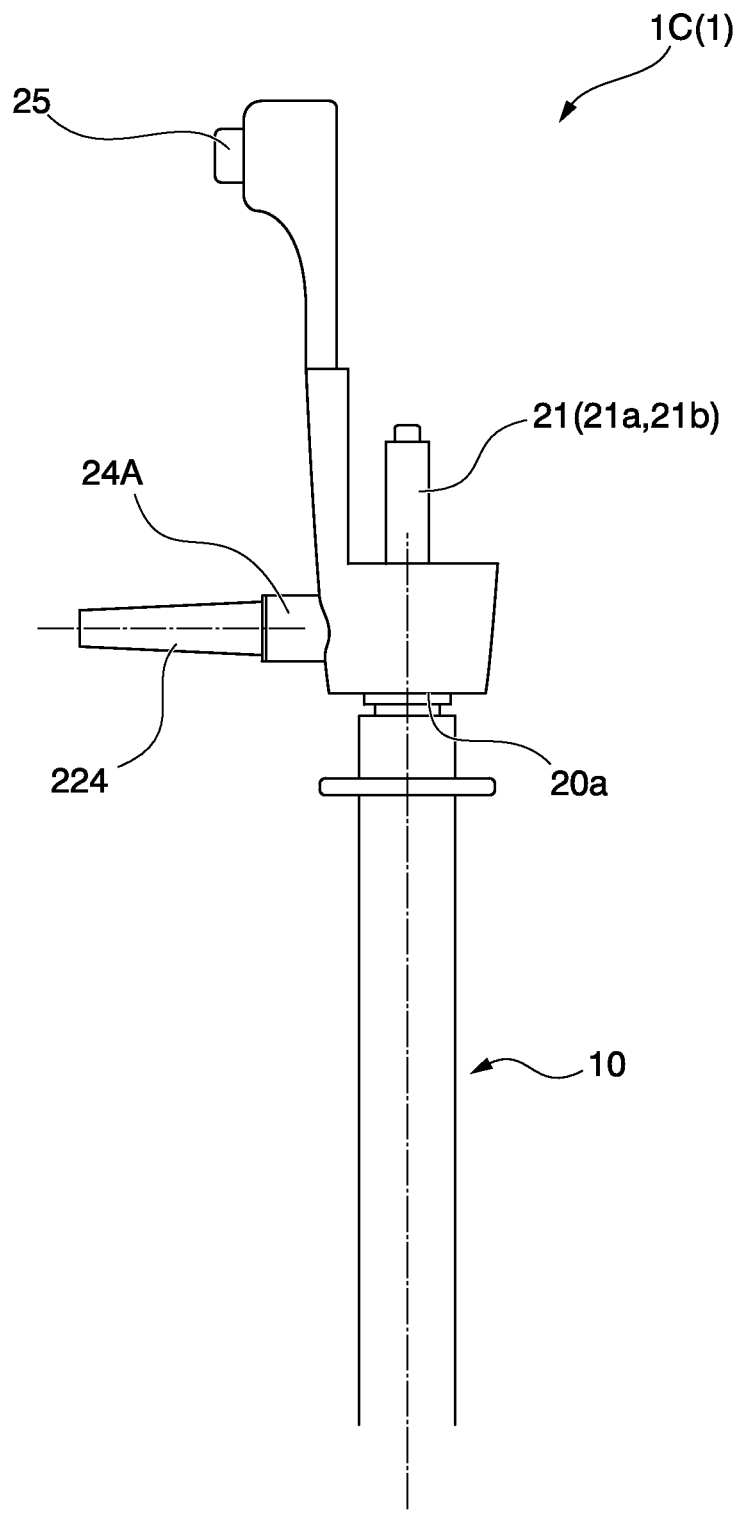
FIG. 14B is a view schematically showing the suction catheter related to the fifth embodiment of the invention and illustrating a structure in which the imaging unit is removed from the control unit.

FIGS. 14A and 14B are views schematically showing a suction catheter 1C (1) related to the fifth embodiment of the invention.

In the suction catheter 1A of the first embodiment and the suction catheter 1B of the second embodiment, the socket 24 and the tube 124 are provided above the adjustment port 25; but, in the suction catheter 1C related to the fifth embodiment, a socket 24A and a tube 224 are provided below the adjustment port 25.

Furthermore, FIG. 14A shows a constitution in which the control unit 20 is connected to the imaging unit 30, and FIG. 14B shows a constitution in which the imaging unit 30 is removed from the control unit 20.

As shown in FIG. 14B, in the case where the imaging unit 30 is removed from the control unit 20, since the terminal connectors 21a and 21b are not connected to the imaging unit 30, the removable portion 21 is exposed.

In the case a user uses the suction catheter 1C, the control unit 20 is covered with a user's hand and user's finger is located at the adjustment port 25.

In a state where the suction device is activated, the adjustment port 25 is operated by the user.

The method of using such suction catheter 1C is the same as that of the aforementioned embodiments.

Accordingly, a distance between the adjustment port 25 and the socket 24A is determined based on a width of a user's clenched hand.

Specifically, in a state where the user holds the control unit 20 so as to be able to press the adjustment port 25, the socket 24A is located below user's little finger.

Therefore, a distance between the adjustment port 25 and the socket 24A is suitably determined based on widths of a user's fingers (forefinger, middle finger, annular finger, and little finger).

In the suction catheter 1C of the above-described fifth embodiment, different from the suction catheter 1A of the first embodiment and the suction catheter 1B of the second embodiment, the socket 24A and the tube 224 are provided at a user's hand holding the control unit 20.

As a result, during use of the suction catheter 1C, the tube 224 does not hinder the operation thereof.

In the suction catheter 1C of the fifth embodiment of the invention, a user holds the control unit 20 near the first space 22 with their hand.

In the suction catheter 1A of the above-mentioned first embodiment, the lighting unit 40 and the imaging module 50 which are weighty are located above a user's hand.

On the other hand, parts of the lighting unit 40 and the imaging module 50 overlap a part of the first space 22 in the present embodiment.

Furthermore, the control unit 20 is connected to the imaging unit 30 so that the removable portion between the control unit 20 and the imaging unit 30 is located between the end 20a of the control unit and the adjustment port 25 or the socket 24A.

As a result of adopting this configuration, when a user grasps the suction catheter 1C, the lighting unit 40 or the imaging module 50 which is weighty is disposed near a user's hand.

Consequently, similar to the aforementioned second embodiment, a balance is stable when the suction catheter 1C is held, and handleability and operability are improved.

Moreover, since a load to be applied to a user's hand in a working state decreases, lessening of fatigue is realized.

As a result, suctioning and removing of the extraneous materials can be effectively carried out in a short amount of time.

While preferred embodiments of the invention have been described and illustrated above, these are exemplary of the invention and are not to be considered as limiting.

Additions, omissions, substitutions of configurations, and other modifications can be made without departing from the scope of the present invention.

The invention is not to be considered as being limited by the foregoing description, and is only limited by the scope of the appended claims.

INDUSTRIAL APPLICABILITY

According to the suction catheter of the present embodiment, extraneous materials such as secretion accumulated in patient's trachea can be easily and effectively removed based on the image that is displayed on the imaging unit without depending on the degree of viscosity thereof.

What is claimed is:

1. A suction catheter comprising:
   a catheter main body that includes a suction passage along a longitudinal direction thereof, a distal end having an opening that corresponds to the suction passage and suctions extraneous materials therethrough, and an end portion on an opposite side of the distal end;
   a handle that is attached to the end portion of the catheter main body;
   an imaging unit that is attachable to and detachable from the handle; and
   an imaging fiber that is arranged inside the catheter main body in a longitudinal direction thereof, passes through the handle, has an end face that is exposed to an outer surface of the handle, and transmits an image that is obtained at the end portion of the catheter main body to the imaging unit, wherein
   the imaging unit comprises a frame, an elastic member, and an imaging module,
   the imaging module consists of a lens and an imaging device, the imaging device image-captures the image transmitted through the end face of the imaging fiber and the lens, the imaging device is controlled by the imaging unit so as to output the captured image as an image signal from the imaging device such that the image signal is transmitted to the imaging unit,
   the imaging unit comprises a removable portion at which the imaging unit is attachable to and detachable from the handle, and the imaging module has a contacting face that comes into contact with the end face of the imaging fiber,
   the elastic member is extendable in a direction parallel to a direction of a force that is applied to the contacting face from the end face of the imaging fiber,
   the elastic member allows the removable portion to press against the handle by generating reactive force in the removable portion,
   the elastic member is provided between part of the frame and part of the imaging module, and
   when the imaging unit is attached to the handle, the elastic member causes part of the imaging module to come into contact with the end face of the imaging fiber, and a position of the imaging module is thereby fixed so that a distance between the lens or the imaging device of the imaging module and the end face of the imaging fiber is constant.

2. The suction catheter according to claim 1, further comprising:
   a light guide that is arranged inside the catheter main body in a longitudinal direction thereof, and transmits illuminating light to the end portion of the catheter main body, wherein
   the illuminating light illuminates the end portion of the catheter main body.

3. The suction catheter according to claim 2, further comprising:
   a light source that is provided at the handle, wherein
   the light source emits the illuminating light, and the illuminating light is thereby incident to the light guide.

4. The suction catheter according to claim 1, wherein
   the imaging unit that comprises the imaging module is attachable to and detachable from an upper portion of the handle.

5. The suction catheter according to claim 1, further comprising:
   a display that is provided at the imaging unit and displays the image captured by the imaging unit.

6. The suction catheter according to claim 1, further comprising:
   a light guide that is arranged inside the catheter main body in a longitudinal direction thereof, and transmits illuminating light to the end portion of the catheter main body;
   a lighting passage that is provided at the catheter main body and in which the light guide is arranged so as to extend along the longitudinal direction of the catheter main body; and
   an imaging pathway that is provided at the catheter main body and in which the imaging fiber is arranged so as to extend along the longitudinal direction of the catheter main body.

7. The suction catheter according to claim 1, wherein
   a position of the imaging module is fixed so that a distance from the end face of the imaging fiber to the imaging device is constant.

8. The suction catheter according to claim 1, wherein
   the imaging module comprises a relay lens, and
   a position of the imaging module is fixed so that a distance from the end face of the imaging fiber to the relay lens is constant.

9. The suction catheter according to claim 1, wherein the elastic member is a spring.

10. A suction catheter comprising:
    a catheter main body that includes a suction passage along a longitudinal direction thereof, a distal end having an opening that corresponds to the suction passage and suctions extraneous materials therethrough, and an end portion on an opposite side of the distal end;
    a handle that is attached to the end portion of the catheter main body;
    an imaging unit that is attachable to and detachable from the handle; and
    an imaging fiber that is arranged inside the catheter main body in a longitudinal direction thereof, passes through the handle, has an end face that is exposed to an outer surface of the handle, and transmits an image that is obtained at the end portion of the catheter main body to the imaging unit, wherein
    the imaging unit comprises a frame, an elastic member, an imaging module, and a lighting unit,
    the imaging module includes an imaging lens and an imaging device, the imaging device image-captures the image transmitted through the end face of the imaging fiber and the imaging lens, the imaging device is controlled by the imaging unit so as to output the captured image as an image signal from the imaging device such that the image signal is transmitted to the imaging unit,
    the lighting unit includes a lighting lens and a light source emitting illuminating light,
    the imaging unit comprises a removable portion at which the imaging unit is attachable to and detachable from the handle, and the imaging module has a contacting face that comes into contact with the end face of the imaging fiber, the elastic member is extendable in a direction parallel to a direction of a force that is applied to the contacting face from the end face of the imaging fiber, the elastic member allows the removable portion to press against the handle by generating reactive force in the removable portion, the elastic member is provided between part of the frame and part of the imaging module, and when the imaging unit is attached to the handle, a position of the end face of the imaging fiber is only displaced in the direction of the force that is applied to the contacting face, a position of the light source is not displaced in a direction of the illuminating light, the elastic member causes part of the imaging module to come into contact with the end face of the imaging fiber, and a position of the imaging module is thereby fixed so that a distance between the imaging lens or the imaging device of the imaging module and the end face of the imaging fiber is constant.

\* \* \* \* \*